United States Patent
Okana et al.

(10) Patent No.: US 6,794,389 B2
(45) Date of Patent: Sep. 21, 2004

(54) QUINAZOLINE DERIVATIVES AND DRUGS

(75) Inventors: Masahiko Okana, Nakaokakyo (JP); Kazuya Mori, Kyoto (JP)

(73) Assignee: Nippon Shinyaku Co., Ltd. (JP)

( * ) Notice: Subject to any disclaimer, the term of this patent is extended or adjusted under 35 U.S.C. 154(b) by 0 days.

(21) Appl. No.: 10/239,750

(22) PCT Filed: Mar. 30, 2001

(86) PCT No.: PCT/JP01/02822
§ 371 (c)(1),
(2), (4) Date: Sep. 25, 2002

(87) PCT Pub. No.: WO01/72710
PCT Pub. Date: Oct. 4, 2001

(65) Prior Publication Data
US 2003/0119855 A1 Jun. 26, 2003

(30) Foreign Application Priority Data

Mar. 31, 2000 (JP) ......................... 2000-098874
Nov. 2, 2000 (JP) ......................... 2000-336464

(51) Int. Cl.⁷ .................. C07D 239/94; C07D 239/84; C07D 239/70; A61K 31/517
(52) U.S. Cl. .................. 514/252.17; 514/266.21; 514/266.23; 514/266.4; 514/267; 544/249; 544/284; 544/291; 544/293
(58) Field of Search ................ 544/249, 284, 544/291, 293; 514/252.17, 266.21, 266.4, 267, 266.23

(56) References Cited

U.S. PATENT DOCUMENTS 3,753,981 A  8/1973  Breuer et al. .......... 260/240 D

FOREIGN PATENT DOCUMENTS

| EP | 1 371 376 A1 | 12/2003 |
|---|---|---|
| JP | 47-2927 | 1/1972 |
| JP | 2923742 | 7/1992 |
| JP | 10-212290 | 8/1998 |
| WO | WO93072124 | 4/1993 |
| WO | WO9720821 | 6/1997 |
| WO | WO9817267 | 4/1998 |
| WO | WO 9850370 | 12/1998 |
| WO | WO9854168 | 12/1998 |
| WO | WO9909986 | 3/1999 |
| WO | WO9948492 A1 | 9/1999 |

Primary Examiner—Deepak Rao
(74) Attorney, Agent, or Firm—Greenberg Traurig LLP; Eugene C. Rzucidlo

(57) ABSTRACT

There is provided an excellent novel analgesic having an analgesic effect which is effective widely against a pain including a chronic pain or an allodynia accompanied with herpes zoster by acting on a nociceptin receptor.

The present invention relates to a compound represented by the following formula:

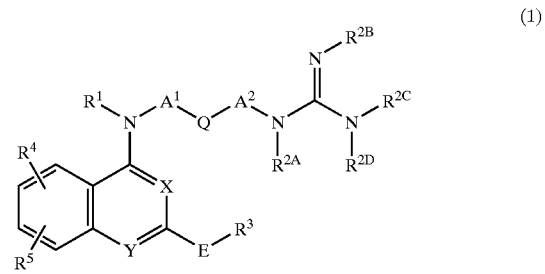

(1)

or a salt thereof.

In the formula, X and Y are same or different and each represents a nitrogen atom or CH; $R^1$ represents a hydrogen atom or alkyl and the like; $A^1$ and $A^2$ are same or different and each represents a single bond or a divalent aliphatic hydrocarbon group; Q represents a single bond, cycloalkylene group, phenylene group or divalent heterocyclic group; $R^{2A}$, $R^{2B}$, $R^{2C}$ and $R^{2D}$ are same or different and each represents a hydrogen atom, alkyl or phenyl; E represents a ethenylene group or —NRCO— (in which R is hydrogen or alkyl) and the like; $R^3$ represents a phenyl group or a heterocyclic group; $R^4$ and $R^5$ are same or different and each represents a hydrogen atom, alkyl, alkoxy, aralkyloxy, halogen, nitro, hydroxy, alkoxycarbonyl, —$NR^6R^7$ (in which $R^6$ and $R^7$ are same or different and each represents a hydrogen atom or alkyl) and the like.

18 Claims, No Drawings

QUINAZOLINE DERIVATIVES AND DRUGS

TECHNICAL FIELD

The present invention relates to a pharmaceutically useful novel heterocyclic derivative or a salt thereof, and a pharmaceutical composition containing the same as an active ingredient.

BACKGROUND ART

As an analgesic, a narcotic analgesic (such as morphine), a non-narcotic analgesic (such as aspirin or indomethacin) or a narco-antagonistic analgesic (such as pentazocine) is employed. A narcotic analgesic exerts its analgesic effect mainly by inhibiting a central algesic excitatory transmission. A non-narcotic analgesic exerts its analgesic effect mainly by inhibiting the production of a peripheral dolorogenic substance. A narco-antagonistic analgesic exerts its analgesic effect in a mechanism similar to that of a narcotic analgesic.

However, there is no analgesic which is effective against a chronic pain which is not suppressed by morphine, an allodynia accompanied with herpes zoster or hyperalgesia, and an excellent analgesic has been desired to be created.

Nociceptin is a neuropeptide related to various nervous activities including an in vivo algesia. Japanese Unexamined Patent Publication No. 10-212290 describes that a nociceptin agonist and/or antagonist may be effective in treating a mental disorder, neuropathy and physiological disorder, and particularly effective in ameliorating anxiety and stress disorder, depression, traumatic disorder, amnesia due to Alzheimer's disease or other dementia, symptoms of epilepsy and spasm, acute and/or chronic pain, drug abuse withdrawal symptoms, water balance control, $Na^+$ excretion, arterial blood pressure disorder, and eating disorder such as an obesity.

As a non-peptide compound acting on a nociceptin receptor, lofentanil, naloxone benzoylhydrazone and 2-oxoimidazole derivative (International Publication WO9854168) are known. However, these compounds are still at the stage of a basic research, and none of them has been commercially available.

As a compound analogous to a quinazoline derivative in the heterocyclic derivatives of the compound according to the present invention, various compounds were known (International Publication WO9307124, Japanese Examined Patent Publication No. 2923742, International Publication WO9720821, International Publication WO9850370, International Publication WO9909986, Japanese Unexamined Patent Publication No. 47-2927, International Publication WO9817267 and the like). Among these, International Publication WO9720821 describes that a 2-acylaminoquinazoline derivative has an inhibitory effect on a neuropeptide Y (NPY) receptor subtype-Y5 and is effective in ameliorating an algesia or amnesia.

DISCLOSURE OF THE INVENTION

An object of the present invention is to provide a novel compound having an excellent analgesic effect. More particularly, the present invention is intended to provide a novel analgesic having an analgesic effect which is effective widely against a chronic pain or an allodynia accompanied with herpes zoster by acting on a nociceptin receptor.

In order to achieve the above described objects, the present inventors found that compound represented by the following general formula (1) is an agonist and/or antagonist of a nociceptin receptor and has an excellent analgesic effect in processes to synthesize and study various compounds, thereby establishing the present invention.

Accordingly, the present invention relates to a compound represented by the following general formula (1):

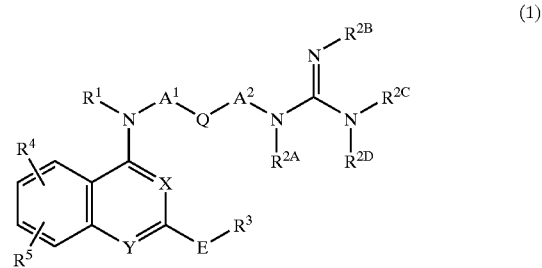

(1)

or a salt thereof.

In the formula, X and Y are same or different and each represents a nitrogen atom or CH;

$R^1$ represents a hydrogen atom or alkyl;

$A^1$ and $A^2$ are same or different and each represents (1) a single bond or (2) a divalent aliphatic hydrocarbon group which may be substituted and which may include 1 to 3 unsaturated bonds at any positions (such aliphatic hydrocarbon group may contain one heteroatom selected from a group consisting of —NH—, O and S);

Q represents (1) a single bond, (2) an optionally substituted 3- to 8-membered cycloalkylene group, (3) an optionally substituted phenylene group or (4) an optionally substituted 4- to 8-membered divalent heterocyclic group;

$R^{2A}$, $R^{2C}$ and $R^{2D}$ are same or different and each represents a hydrogen atom, alkyl or phenyl, $R^{2B}$ represents a hydrogen atom, alkyl, cyano, nitro or phenyl, or a two nitrogen atoms of a guanidino group are cyclized together with one or two of its substituents $R^{2B}$, $R^{2C}$ and $R^{2D}$ to form a saturated or unsaturated 5- or 6-membered ring;

or is taken together as —N($R^1$)—$A^1$—Q–$A^2$—N($R^{2A}$)— to form a 5- to 7-membered ring;

E represents (1) ethenylene, (2) —NRCO—, (3) —NRCONH—, (4) —CONR—, (5) ethynylene, (6) —$NRSO_2$— or (7) aminoalkylene (in which R represents hydrogen or optionally substituted alkyl);

$R^3$ represents an optionally substituted phenyl group or heterocyclic group;

$R^4$ and $R^5$ (1) are same or different and each represents a hydrogen atom, alkyl, alkoxy, aralkyloxy, halogen, nitro, hydroxy, alkoxycarbonyl, —$NR^6R^7$, —$NR^6COR^7$, —$NR^6SO_2R^7$, —$CONR^6R^7$ (in which $R^6$ and $R^7$ are same or different and each represents a hydrogen atom or alkyl) or (2) when adjacent to each other are taken together to form —$O(CH_2)_nO$— (wherein n is an integer of 1 or 2) or —CH═CH—CH═CH—.

Preferably, in the formula (1), each of X and Y represents a nitrogen atom or CH;

$R^1$ represents a hydrogen atom or alkyl;

$A^1$ and $A^2$ are same or different and each represents (1) a single bond or (2) alkylene which may be substituted by alkyl, carbamoyl, monoalkylcarbamoyl, dialkylcarbamoyl, hydroxy, alkoxy or trifluoromethyl and which may have 1 to 3 unsaturated bonds at any positions;

Q represents (1) a single bond, (2) a 3- to 8-membered cycloalkylene group which may be substituted by alkyl, alkoxycarbonyl, carbamoyl, monoalkylcarbamoyl, dialkylcarbamoyl or alkoxy, (3) a phenylene group which may be substituted by alkyl, alkoxy, alkoxycarbonyl, carbamoyl, monoalkylcarbamoyl, dialkylcarbamoyl, sulfamoyl, monoalkylsulfamoyl, dialkylsulfamoyl, amino, monoalkylamino, dialkylamino, nitro, halogen, cyano or trifluoromethyl, or (4) a 4- to 8-membered divalent heterocyclic group which may be substituted by alkyl, alkoxy, alkoxycarbonyl, carbamoyl, monoalkylcarbamoyl, dialkylcarbamoyl, amino, monoaklylamino or dialkylamino;

$R^{2A}$, $R^{2C}$ and $R^{2D}$ are same or different and each represents a hydrogen atom, alkyl or phenyl, $R^{2B}$ represents a hydrogen atom, alkyl, cyano group, nitro group or phenyl, or a two nitrogen atoms of a guanidino group are cyclized together with one or two of its substituents $R^{2B}$, $R^{2C}$ and $R^{2D}$ to form a saturated or unsaturated 5- or 6-membered ring;

or is taken together as $-N(R^1)-A^1-Q-A^2-N(R^{2A})-$ to form a 5- to 7-membered ring;

E represents (1) ethenylene, (2) —NRCO—, (3) —NRCONH—, (4) —CONR—, (5) ethynylene, (6) —NRSO$_2$— or (7) aminoalkylene (in which R represents hydrogen or optionally substituted alkyl);

$R^3$ represents a phenyl group or heterocyclic group which may be substituted by alkyl, alkoxy, alkoxycarbonyl, carbamoyl, monoalkylcarbamoyl, dialkylcarbamoyl, sulfamoyl, monoalkylsulfamoyl, dialkylsulfamoyl, alkylsulfonylamino, N-(alkyl)alkylsulfonylamino, amino, monoalkylamino, dialkylamino, nitro, halogen, cyano, hydroxy or trifluoromethyl; and $R^4$ and $R^5$ (1) are same or different and each represents a hydrogen atom, alkyl, alkoxy, aralkyloxy, halogen, nitro, hydroxy, alkoxycarbonyl, $-NR^6R^7$, $-NR^6COR^7$, $-NR^6SO_2R^7$, $-CONR^6R^7$ (in which $R^6$ and $R^7$ are same or different and each represents a hydrogen atom or alkyl) or (2) when adjacent to each other are taken together to form $-O(CH_2)_nO-$ (wherein n represents an integer of 1 or 2) or —CH=CH—CH=CH—.

A more preferable compound is represented by the general formula (1), wherein each of X and Y is a nitrogen atom, $R^1$ is a hydrogen atom or alkyl, $A^1$ and $A^2$ are same or different and each is (1) a single bond or (2) optionally substituted alkylene, Q is (1) a single bond, (2) an optionally substituted 4- to 8-membered cycloalkylene group (3) an optionally substituted phenylene group or (4) an optionally substituted 5- to 7-membered divalent heterocyclic group, $R^{2A}$, $R^{2B}$, $R^{2C}$ and $R^{2D}$ are same or different and each is a hydrogen atom, alkyl or phenyl, or taken together as $-N(R^1)-A^1-Q-A^2-N(R^{2A})-$ to form a 5- to 7-membered ring, E is (1) ethenylene, (2) —NRCO— or (3) —CONR—, and $R^4$ and $R^5$ (1) are same or different and each represents a hydrogen atom, alkyl, alkoxy, aralkyloxy, halogen, nitro, hydroxy or alkoxycarbonyl or (2) when adjacent to each other are taken together to form $-O(CH_2)_nO-$ (wherein n is an integer of 1 or 2) or —CH=CH—CH=CH—.

A further preferable compound is represented by the general formula (1), wherein each of X and Y is a nitrogen atom, $R^1$ is a hydrogen atom, $A^1$ and $A^2$ are same or different and each is (1) a single bond or (2) optionally substituted alkylene, Q is (1) a single bond, (2) an optionally substituted 5- to 7-membered cycloalkylene group or (3) an optionally substituted phenylene group, $R^{2A}$, $R^{2B}$, $R^{2C}$ and $R^{2D}$ are same or different and each is a hydrogen atom, alkyl or phenyl, E is (1) ethenylene or (2) —NRCO—, and $R^4$ and $R^5$ are same or different and each is a hydrogen atom, alkyl, alkoxy, aralkyloxy, halogen or nitro.

The present invention further relates to a pharmaceutical composition including any of those compounds mentioned above or a salt thereof, and more particularly to an analgesic.

A structual feature of a compound of the present invention is as follows: the presence of a guanidino group at the end of the substituent, $-N(R^1)-A^1-Q-A^2-$, in the 4-position of a quinazoline or quinoline skeleton or 1-position of the isoquinoline skeleton; or the cyclization of two NHs in the ganidino group together with a substituent thereon.

A compound according to the present invention, which has the feature described above, is a novel compound which was not found in references. A compound according to the present invention acts on a nociceptin receptor thereby exerting an excellent analgesic effect.

The present invention will be detailed below.

Examples of an "alkyl" in the present invention may include a straight or branched alkyl having 1 to 6 carbon atoms, for example, methyl, ethyl, n-propyl, isopropyl, n-butyl, isobutyl, sec-butyl, tert-butyl, n-pentyl, 5-isopentyl, n-hexyl, isohexyl and the like. Particularly, alkyl having 1 to 4 carbon atoms is preferable.

Examples of "alkoxy" may include a straight or branched alkoxy having 1 to 6 carbon atoms, for example, methoxy, ethoxy, n-propoxy, isopropoxy, n-butoxy, isobutoxy, sec-butoxy, tert-butoxy, n-pentyloxy, isopentyloxy, n-hexyloxy, isohexyloxy and the like. Particularly, alkoxy having 1 to 4 carbon atoms is preferable.

Examples of "aralkyloxy" may include aralkyloxy having 7 to 10 carbon atoms, for example, benzyloxy, phenetyloxy and the like. Particularly, benzyloxy is preferable.

Examples of a "divalent aliphatic hydrocarbon group" may include a straight or branched alkylene having 1 to 6 carbon atoms (for example, methylene, ethylene, trimethylene, tetramethylene, pentamethylene, hexamethylene, 2-ethyltrimethylene and 1-methyltetramethylene), a straight or branched alkenylene having 2 to 6 carbon atoms (for example, vinylene and propenylene) or a straight or branched alkynylene having 2 to 6 carbon atoms (for example, ethynylene). Such an aliphatic hydrocarbon group may contain one heteroatom selected from a group consisting of NH, oxygen atom and sulfur atom.

Examples of the alkylene in an "aminoalkylene" may include an alkylene listed in the "divalent aliphatic hydrocarbon group".

Examples of a "cycloalkylene" may include cycloalkylene having 3 to 8 carbon atoms, for example, cyclopropylene, cyclobutylene, cyclopentylene, cyclohexylene, cycloheptylene and cyclooctylene. Such a cycloalkylene may have 1 to 2 substituents, and an example of such substituents may include alkyl, alkoxycarbonyl, carbamoyl, monoalkylcarbamoyl, dialkylcarbamoyl or alkoxy. It may also contain an unsaturated bond, and examples of cycloalkylene containing such an unsaturated bond include cyclohexenylene, cycloheptenylene, cyclooctenylene and the like.

Examples of a "halogen" may include fluorine, chlorine, bromine and iodine atoms.

Examples of a heterocyclic ring in a "heterocyclic group" and "divalent heterocyclic group" may include a 4-to 8-membered monocyclic or fused ring which contains 1 to 2 heteroatoms selected from a group consisting of NH, oxygen atom and sulfur atom, and which may have 1 to 4 unsaturated bonds. Examples of $R^3$ may include 2-pyridyl, 3-pyridyl, 4-pyridyl, 2-pyrimidinyl, 4-pyrimidinyl, 5-pyrimidinyl, 3-pyridazinyl, 4-pyridazinolyl, 2-pyrazinyl and 3-pyrazinyl. Such a heterocyclic group may have 1 to 2 substituents, and examples of the substituents may include alkyl, alkoxy, alkoxycarbonyl, carbamoyl, monoalkylcarbamoyl, dialkylcarbamoyl, sulfamoyl, monoalkylsulfamoyl, dialkylsulfamoyl, alkylsulfonylamino, N-(alkyl)alkylsulfonylamino, amino, monoalkylamino, dialkylamino, nitro, halogen, cyano, hydroxy or trifluoromethoxy. Examples of a heterocyclic ring in a heterocyclic group Q may include pyridine, pyrimidine, piperazine, homopiperazine, furan, thiophene and the like. The heterocyclic group Q may have 1 to 2 substituents, and examples of such substituents may include alkyl, alkoxy, alkoxycarbonyl, carbamoyl, monoalkylcarbamoyl, dialkylcarbamoyl, amino, monoalkylamino or dialkylamino.

A "phenylene group" may have 1 to 2 substituents, and examples of such substituents may include alkyl, alkoxy, alkoxycarbonyl, carbamoyl, monoalkylcarbamoyl, dialkylcarbamoyl, sulfamoyl, monoalkylsulfamoyl, dialkylsulfamoyl, amino, monoalkylamino, dialkylamino, hydroxy, nitro, halogen, cyano and trifluoromethyl.

An example of a ring represented by $-N(R^1)-A^1-Q-A^2-N(R^{2A})-$ may include a 5- to 7-membered saturated ring, such as piperazino or homopiperazino.

Examples of a "salt" of the compound (1) encompassed in the present invention may include a salt with an inorganic acid such as hydrochloric acid, sulfuric acid, nitric acid, phosphoric acid, hydrofluoric acid or hydrobromic acid, or a salt with an organic acid such as acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid or camphorsulfonic acid.

Examples of a particularly preferred compound may include (1S,2R)-N-amidino-2-{[2-(4-chlorobenzoylamino)-6-methoxyquinazolin-4-yl]amino}cyclohexylamine dihydrochloride, N-amidino-2-[6-methoxy-4-{2-[2-(2-pyridyl)ethenyl]quinazolin-4-yl}aminoethyl]phenylethylamine trihydrochloride, cis-4-guanidinomethyl-cis-2-methyl-N-{6-methoxy-2-[2-(2-pyridyl)ethenyl]quinazolin-4-yl}cyclohexylamine trihydrochloride, N-amidino-N'-{6-methyl-2-[2-(2-pyridyl)ethenyl]quinazolin-4-yl}-1,6-hexanediamine trihydrochloride, (1S,2R)-cis-N-amidino-2-{[2-(4-chlorostyryl)-6-methoxyquinazolin-4-yl]amino}cyclohexylamine dihydrochloride and N-amidino-N'-{6-methoxy-2-[2-(2-pyridyl)ethenyl]quinazolin-4-yl}-1,6-hexanediamine trihydrochloride.

A compound according to the present invention may exist as a cis (Z form) isomer or a trans (E form) isomer, and each isomer and a mixture thereof are also included in the present invention.

Some of the compounds according to the present invention may have asymmetric carbon atoms, and each optical isomer and a racemate thereof are also included in the present invention. An optical isomer can be produced, for example, by starting from a racemate obtained as described above utilizing the basic property thereof using an optically active acid (tartaric acid, dibenzoyltartaric acid, mandelic acid, 10-camphorsulfonic acid and the like) by a known method to effect an optical resolution, or by starting from a previously prepared optically active compound.

The compound (1) according to the present invention can be produced, for example, by the following methods.

Production Method A

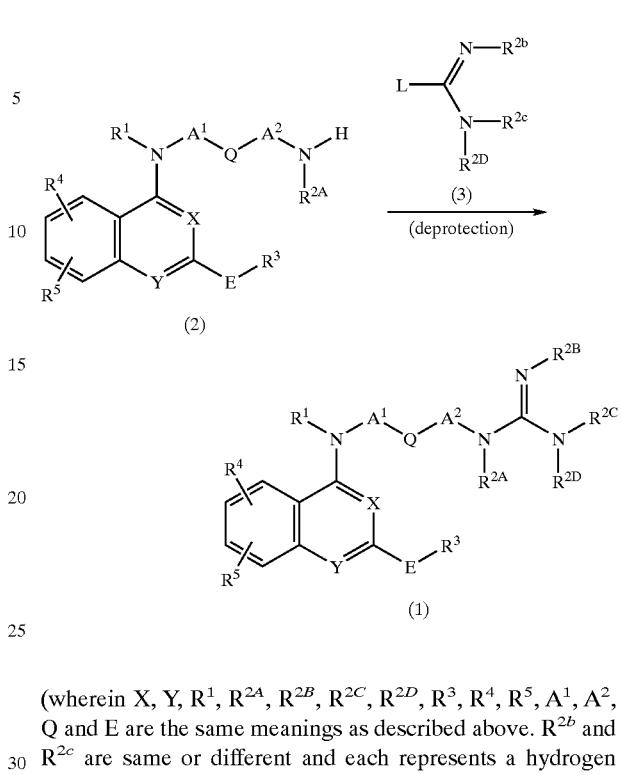

(wherein X, Y, $R^1$, $R^{2A}$, $R^{2B}$, $R^{2C}$, $R^{2D}$, $R^3$, $R^4$, $R^5$, $A^1$, $A^2$, Q and E are the same meanings as described above. $R^{2b}$ and $R^{2c}$ are same or different and each represents a hydrogen atom, alkyl, phenyl, cyano, nitro or a protective group. L represents a leaving group.)

Examples of a protective group may include tert-butoxycarbonyl, benzyloxycarbonyl, benzyl and the like. Examples of a leaving group may include pyrazol-1-yl, methylthio, methoxy, halogen and the like. A compound (2) is reacted with one equivalent to excess amount of a compound (3) in hydrocarbons such as benzene and toluene, ethers such as dioxane and tetrahydrofuran, halogenated-hydrocarbons such as chloroform, methylene chloride and 1,2-dichloroethane or in N,N-dimethylformamide at a temperature from 0° C. to the boiling point of the employed solvent for several hours to several days followed by deprotecting $R^{2b}$ and $R^{2c}$, when being present as protective groups, by a method known per se, thereby obtaining the compound (1). It is preferred particularly to employ pyrazol-1-yl as a leaving group L on the compound (3) and tert-butoxycarbonyl as a protective group, 1,2-dichloroethane as a solvent, and to effect the reaction at room temperature for 1 to 48 hours followed by the deprotection with hydrochloric acid.

Production Method B (When $R^{2B}$ in the Compound (1) is a Hydrogen Atom)

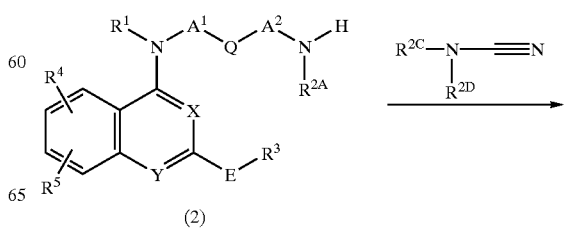

-continued

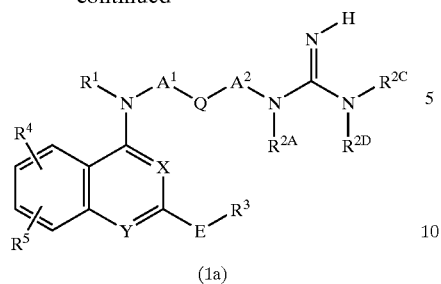

(1a)

(wherein X, Y, $R^1$, $R^{2A}$, $R^{2B}$, $R^{2C}$, $R^{2D}$, $R^3$, $R^4$, $R^5$, $A^1$, $A^2$, Q and E are the same meanings as described above.)

A compound (1a) can be produced by reacting the compound (2) with $R^{2C}R^{2D}N$—CN by a known method (J. Med. Chem. 18, 90, 1975 and the like).

Production Method C (When $R^{2D}$ in the Compound (1) is a Hydrogen Atom)

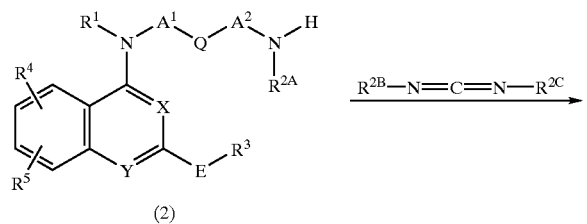

(2)

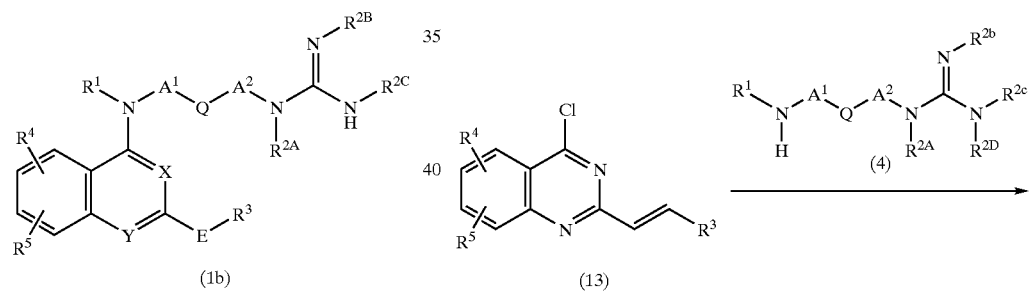

(1b)

(wherein X, Y, $R^1$, $R^{2A}$, $R^{2B}$, $R^{2C}$, $R^3$, $R^4$, $R^5$, $A^1$, $A^2$, Q and E are the same meanings as described above.)

The compound (1b) can be produced by reacting the compound (2) with $R^{2B}$—N=C=N—$R^{2C}$ by a known method (J. Am. Chem. Soc., 3673, 1962 and the like).

Production Method D

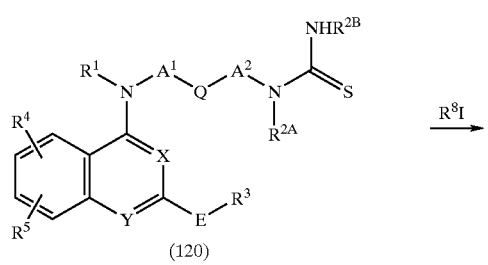

(120)

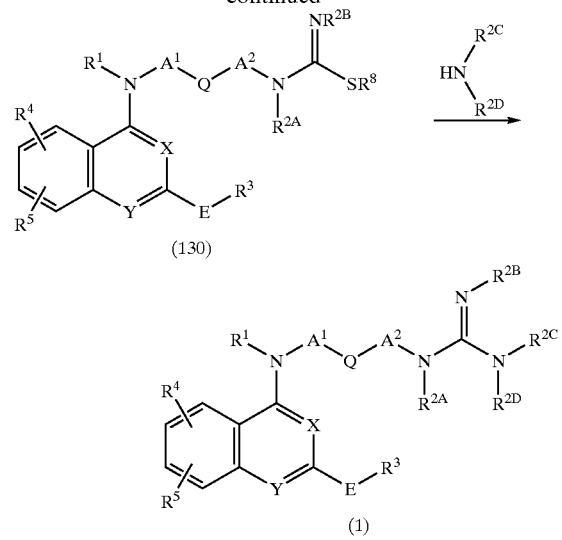

(1)

(wherein X, Y, $R^1$, $R^{2A}$, $R^{2B}$, $R^{2C}$, $R^{2D}$, $R^3$, $R^4$, $R^5$, $A^1$, $A^2$, Q and E are the same meanings as described above. $R^8$ represents an alkyl.)

The compound (1) can be produced from a compound (120) by a known method (Synthesis, 6, 460, 1988 and the like). An alkyl as $R^8$ is an alkyl having 1 to 4 carbon atoms, and is preferably methyl.

Production Method E

A compound (1A) which is the compound (1) wherein E is ethenylene, X and Y are both N can be produced by the reaction process shown below.

(wherein $R^1$, $R^{2A}$, $R^{2B}$, $R^{2C}$, $R^{2D}$, $R^3$, $R^4$, $R^5$, $A^1$, $A^2$, $R^{2b}$, $R^{2c}$ and Q are the same meanings as described above.)

A compound (13) is reacted with one equivalent to excess amount of an amine (4) in the presence of a base such as sodium hydride or N,N-diisopropylethylamine in a solvent having a high boiling point such as 1-pentanol, N,N-dimethylformamide or phenol, at a temperature from 50° C. to the boiling point of the employed solvent for several hours to several days followed by deprotecting $R^{2b}$ and $R^{2c}$, when being present as protective groups, by a method known per se, thereby obtaining the compound (1A). Preferably, the reeaction is carried out in phenol at 150° C. to 180° C. for 5 to 24 hours followed by deprotection using hydrochloric acid to obtain the compound (1A).

Production Method F

A compound (1Z) which is the compound (1) wherein E is —NRCO— and X and Y are both N can be produced also by the reaction process shown below.

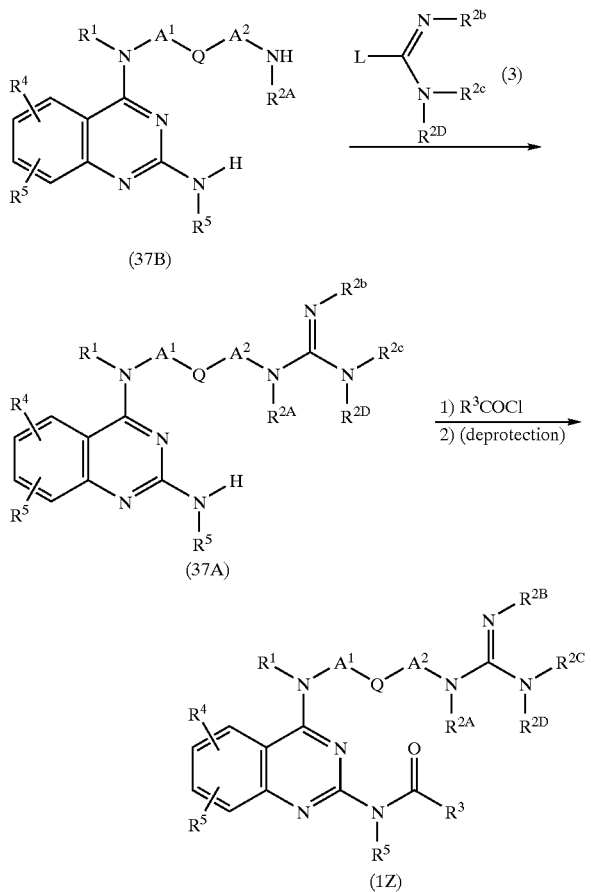

(wherein R, $R^1$, $R^{2A}$, $R^{2B}$, $R^{2C}$, $R^{2D}$, $R^3$, $R^4$, $R^5$, $A^1$, $A^2$, $R^{2b}$, $R^{2c}$ and Q are the same meanings as described above.)

A compound (37B) is reacted with one equivalent to excess amount of the compound (3) in hydrocarbons such as benzene and toluene, ethers such as dioxane and tetrahydrofuran, halogenated-hydrocarbones such as chloroform, methylene chloride and 1,2-dichloroethane or in N,N-dimethylformamide at a temperature from 0° C. to the boiling point of the employed solvent for several hours to several days, thereby obtaining a compound (37A). It is preferred particularly to employ pyrazol-1-yl as a leaving group L on the compound (3) and tert-butoxycarbonyl as a protective group, 1,2-dichloroethane as a solvent.

The compound (37A) is reacted with one equivalent to excess amount of an acid chloride in hydrocarbons such as benzene and toluene, ethers such as dioxane and tetrahydrofuran, halogenated-hydrocarbons such as methylene chloride, 1,2-dichloroethane and chloroform in the presence of a base such as triethylamine, N,N-diisopropylethylamine or pyridine if necessary using a catalyst such as 4-dimethylaminopyridine at a temperature from room temperature to the boiling point of the employed solvent for several hours to several days followed by deprotecting $R^{2b}$ and $R^{2c}$, when being present as protective groups, by a method known per se, thereby obtaining the compound (1Z).

The compound (1) thus produced can be isolated and purified by a method known per se, such as concentration, liquid phase conversion, partition, solvent extraction, crystallization, recrystallization, fractional distillation or chromatography.

A starting compound (2) can be produced in accordance with the following reaction scheme.

(a) When E is Ethenylene and X and Y are Both N in the Compound (2)

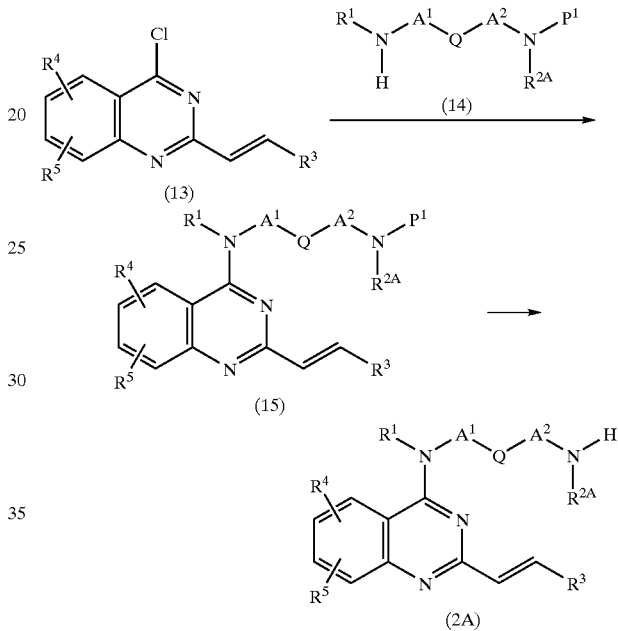

(wherein $R^1$, $R^{2A}$, $R^3$, $R^4$, $R^5$, $A^1$, $A^2$ and Q are the same meanings as described above. $P^1$ represents a protective group.)

Examples of a protective group may include tert-butoxycarbonyl, benzyloxycarbonyl and the like.

A compound (13) (obtained similarly to in page 13 to 15 in International Publication WO9909986) is reacted with one equivalent to excess amount of an amine (14) in hydrocarbons such as benzene and toluene, ethers such as dioxane and tetrahydrofuran, alcohols such as ethanol and isopropanol, or in an organic solvent such as N,N-dimethylformamide, if necessary in the presence of a base such as triethylamine or N,N-diisopropylethylamine, at a temperature from room temperature to the boiling point of the employed solvent for several hours to several days followed by deprotection with hydrochloric acid, trifluoroacetic acid or by hydrogenation with palladium/carbon, thereby obtaining a compound (2A). It is preferred particularly that the compound (13) is reacted with 1 to 2 equivalents of an amine (14) wherein $P^1$ is tert-butoxycarbonyl in toluene as a solvent in the presence of triethylamine (TEA) at 100° C. to 130° C. for 24 to 48 hours and then deprotection is effected with hydrochloric acid.

(b) When E is Ethenylene, X is CH, Y is N in the Compound (2)

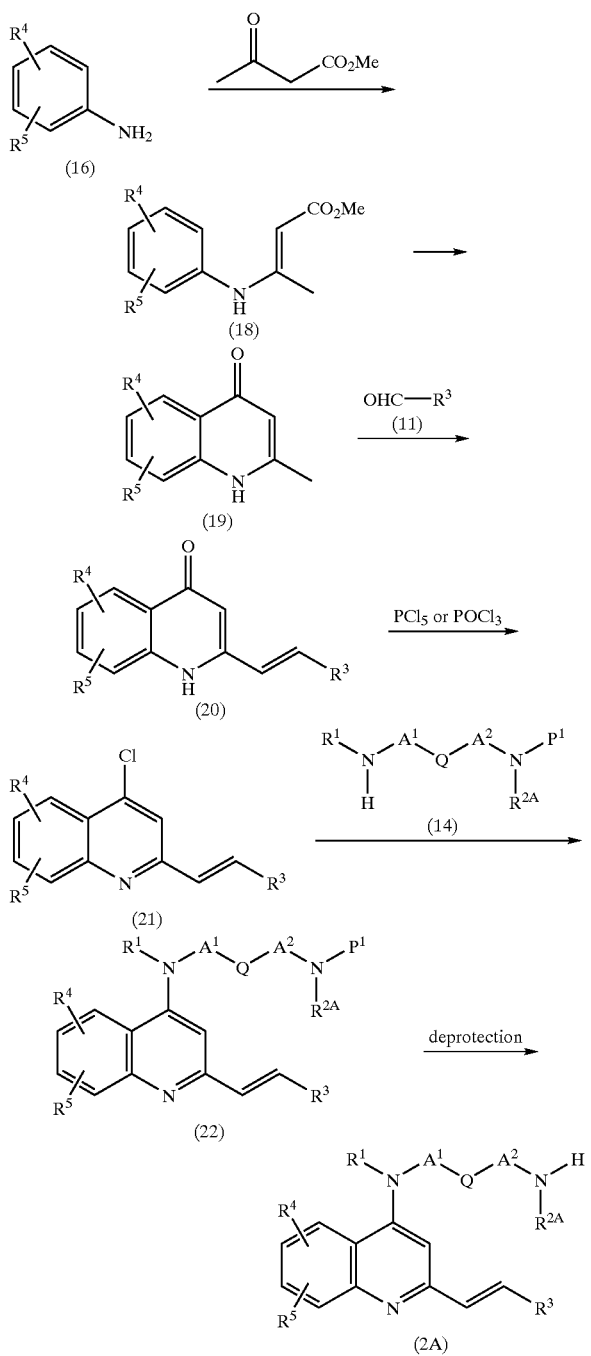

(wherein $R^1$, $R^{2A}$, $R^3$, $R^4$, $R^5$, $A^1$, $A^2$, Q and $P^1$ are the same meanings as described above.)

Starting from a compound (16), a known method (see JACS 70, 4065 (1948); JACS 70, 2402 (1948); JOC 12, 456 (1947) and the like) is employed to produce a compound (19).

The compound (19) is reacted with an aldehyde (11) in a solvent such as acetic anhydride, acetic acid or trifluoroacetic acid at a temperature from room temperature to the boiling point of the employed solvent for 1 to 48 hours, preferably in acetic anhydride as a solvent at 80° C. to 100° C. for 5 to 24 hours, thereby obtaining a compound (20). The aldehyde (11) may be commercially available or can be produced by a known method.

The compound (20) is reacted with a chlorinating agent such as phosphorus oxychloride or phosphorus pentachloride without using any solvent or in a solvent such as toluene, xylene or 1,2-dichloroethane at a temperature from room temperature to the boiling point of the employed solvent, or a temperature from room temperature to the boiling point of the chlorinating agent employed in case where no solvent is used, for 1 to 24 hours, thereby obtaining a compound (21). In this procedure, a tertiary amine such as dimethylaniline or triethylamine may be present if necessary.

The compound (21) is reacted with one equivalent to excess amount of the amine (14) in the above-described (a), and then deprotected if necessary by a method known per se to obtain a compound (2B). It is preferred particularly that the compound (21) is reacted with 1 to 2 equivalents of the amine (14) wherein $P^1$ is tert-butoxycarbonyl in toluene as a solvent in the presence of triethylamine at 100° C. to 130° C. for 24 to 48 hours to obtain a compound (22) which is then deprotected with trifluoroacetic acid in methylene chloride.

(c) When E is Ethenylene, X is N and Y is CH in the Compound (2)

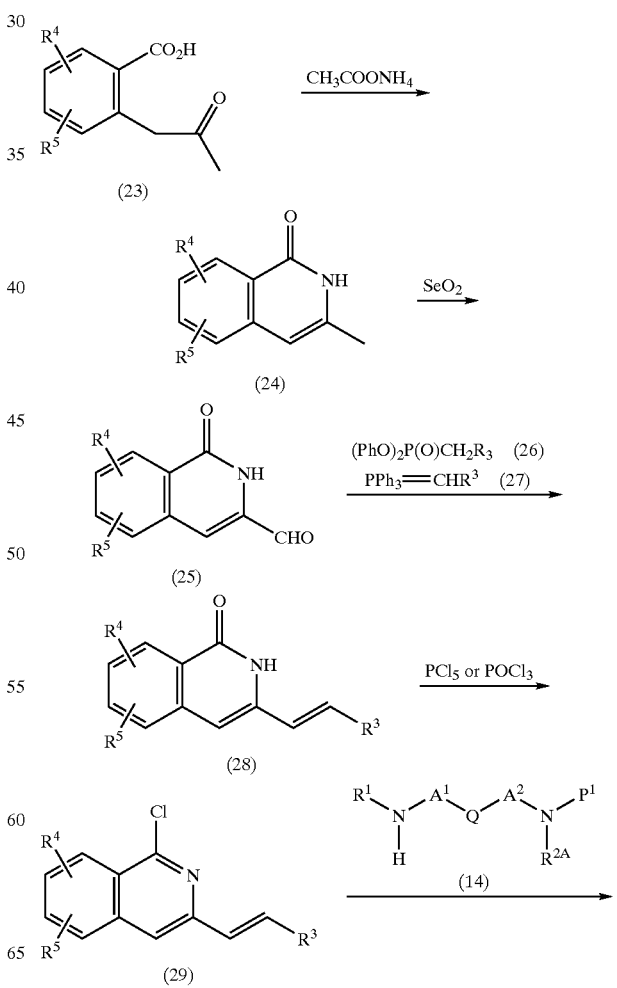

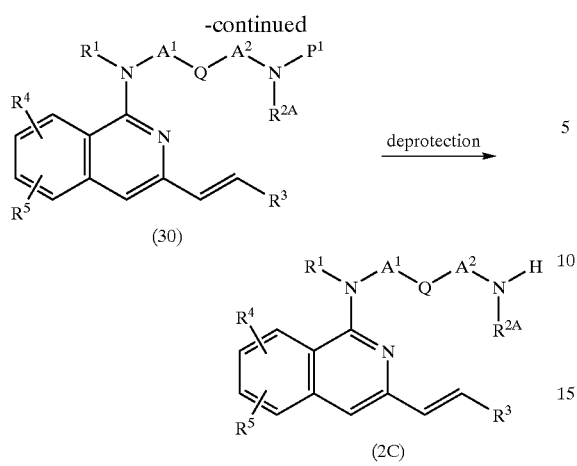

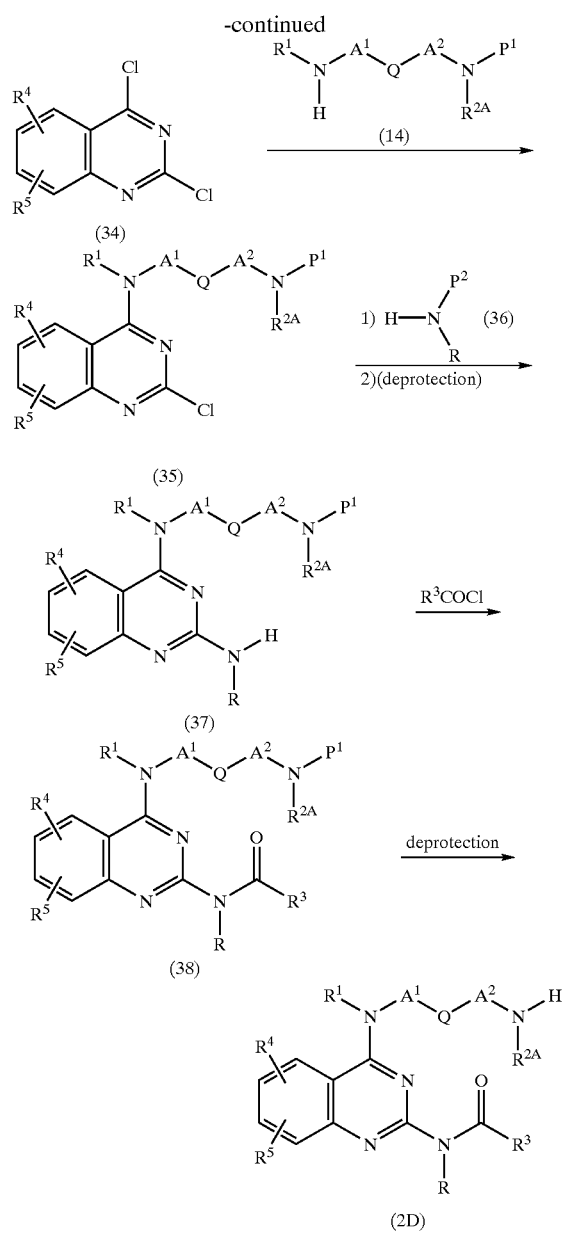

(wherein $R^1$, $R^{2A}$, $R^3$, $R^4$, $R^5$, $A^1$, $A^2$, Q and $P^1$ are the same meanings as described above.)

Starting from a compound (23), a known method (J. Chem. Soc. Perkin Trans 1, 1990, 1770) is employed to produce a compound (24).

The compound (24) is reacted with 1 to 3 equivalents of selenium dioxide in ethers such as dioxane and tetrahydrofuran, or alcohols such as ethanol and isopropanol at a temperature from room temperature to the boiling point of the employed solvent for several hours to several days, preferably in dioxane at 50° C. to 100° C. for 5 to 48 hours, thereby obtaining a compound (25).

The compound (25) is reacted with a compound (26) or a compound (27) in a solvent which does not participate in the reaction such as dioxane or tetrahydrofuran, in the presence of a base such as n-butyllithium, sodium hydride or sodium hexamethyl disilazide at a temperature from −78° C. to the boiling point of the employed solvent for several hours to several days, preferably in tetrahydrofuran at a temperature from −20° C. to room temperature for 1 to 5 hours, thereby obtaining a compound (28).

Similarly to the procedure in the above-described (b), the compound (28) is reacted with a chlorinating agent such as phosphorus oxychloride or phosphorus pentachloride for 1 to 24 hours to obtain a compound (29). The compound (29) is reacted with one equivalent to excess amount of the amine (14) in the above-described (a) and then deprotected if necessary by a method known per se to obtain a compound (2C).

(d) When E is —NRCO— and X and Y are Both N in the Compound (2)

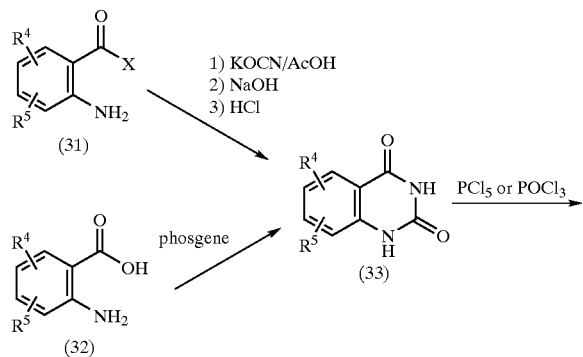

(wherein R, $R^1$, $R^{2A}$, $R^3$, $R^4$, $R^5$, $A^1$, $A^2$, Q and $P^1$ are the same meanings as described above. X represents a hydroxy group or amino group. $P^2$ represents a hydrogen atom or a protective group such as benzyl or 4-methoxybenzyl).

A compound (34) can be produced from the compounds (31) and (32) in accordance with a known method (Japanese Patent No. 2923742).

The compound (34) is reacted with one equivalent to excess amount of the amine (14) in the same solvent as that of the above-described (a) if necessary in the presence of a base such as triethylamine or N,N-diisopropylethylamine at a temperature from 0° C. to the boiling point of the employed solvent for several hours to several days, preferably in the presence of triethylamine at room temperature for 5 to 48 hours to obtain a compound (35).

The compound (35) is reacted with one equivalent to excess amount of an amine (36) in a solvent having a high boiling point such as phenol or diphenyl ether, if necessary in the presence of a base such as triethylamine or N,N-diisopropylethylamine at a temperature from room temperature to the boiling point of the employed solvent for several hours to several days, or in hydrocarbons such as benzene, toluene and xylene, ethers such as dioxane and tetrahydrofuran, in the presence of a metal catalyst such as palladium acetate, a ligand such as 2,2'-bis(diphenylphosphino)-1,1'-binaphthyl and a base such as sodium tert-butoxide at a temperature from room temperature to the boiling point of the employed solvent for several hours to several days, and followed by deprotecting $P^2$ when being present as a protective group by a method having no effect on $P^1$, whereby obtaining a compound (37).

The compound (37) is reacted with one equivalent to excess amount of an acid chloride in hydrocarbons such as benzene and toluene, ethers such as dioxane and tetrahydrofuran, halogenated hydrocarbons such as methylene chloride, 1,2-dichloroethane and chloroform in the presence of a base such as triethylamine, N,N-diisopropylethylamine or pyridine if necessary using a catalyst such as 4-dimethylaminopyridine at a temperature from room temperature to the boiling point of the employed solvent for several hours to several days, thereby obtaining a compound (38). The compound (38) is deprotected by a method known per se to obtain a compound (2D). It is preferred particularly to effect the reaction using methylene chloride as a solvent in the presence of triethylamine using a catalytic amount of 4-dimethylaminopyridine at room temperature for 24 to 48 hours. The acid chloride may be commercially available or can be produced by a known method.

(e) When E is —NHCO— and X and Y are Both N in the Compound (2)

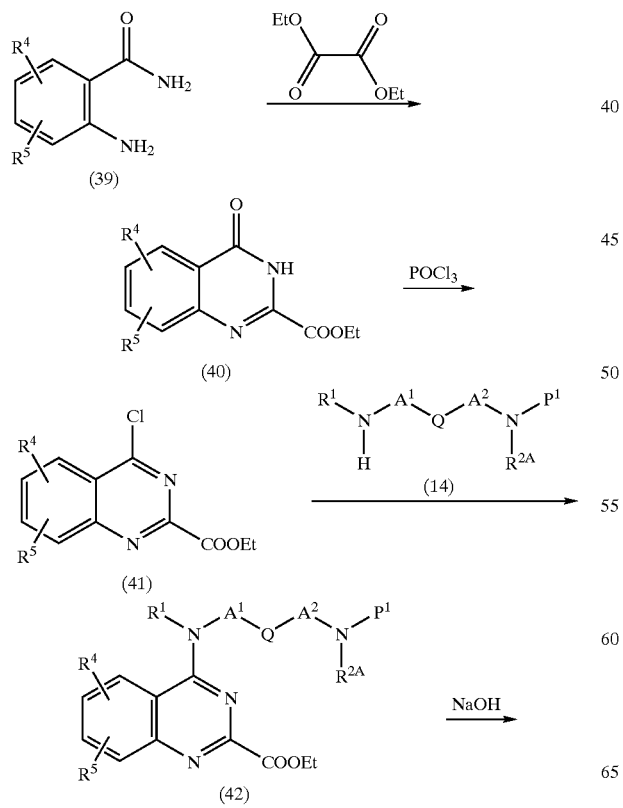

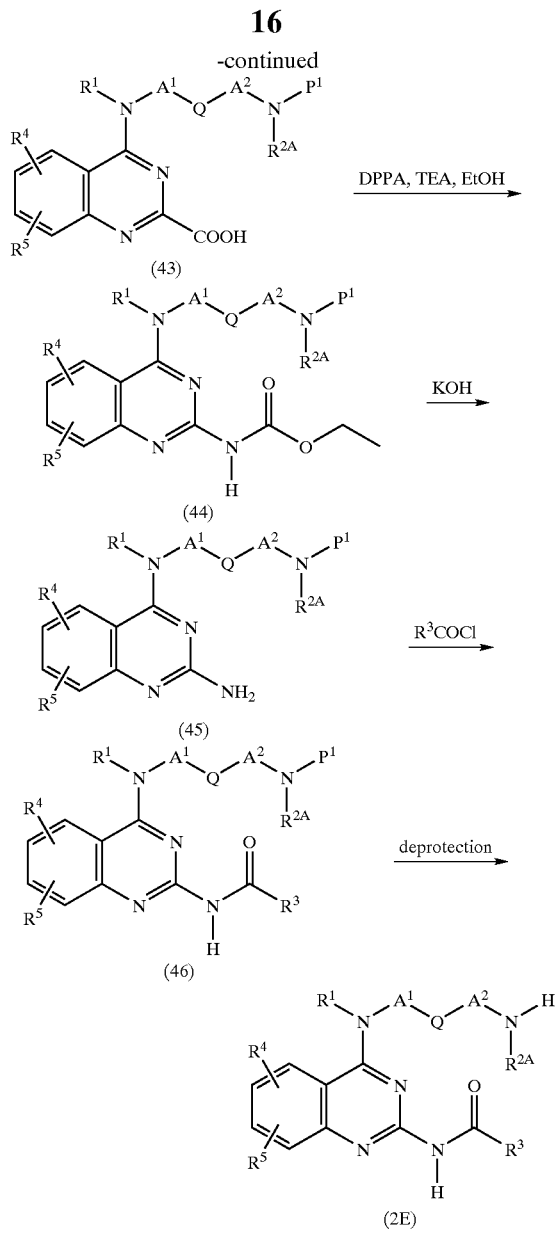

(wherein $R^1$, $R^{2A}$, $R^3$, $R^4$, $R^5$, $A^1$, $A^2$, Q and $P^1$ are the same meanings as described above.)

Starting from a compound (39), a known method (see JOC 27, 4672 (1962)) is employed to obtain a compound (41).

The compound (41) is reacted with one equivalent to excess amount of the amine (14) as similar to the above-described (a) to obtain a compound (42). It is preferred particularly to react the compound (41) with 1 to 2 equivalents of the amine (14) in toluene as a solvent in the presence of triethylamine (TEA) at 100° C. to 130° C. for 24 to 48 hours.

By hydrolyzing the compound (42) by a method known per se, a compound (43) is obtained. It is preferred particularly to react the compound (42) in ethanol in the presence of a 1N aqueous solution of sodium hydroxide at room temperature to 60° C. for 1 to 3 hours.

The compound (43) is reacted with diphenylphosphoryl azide (DPPA) in alcohols such as ethanol and benzyl alcohol in the presence of a base such as triethylamine or N,N-diisopropylethylamine at a temperature from room temperature to the boiling point of the employed solvent for several hours to several days, thereby obtaining a compound (44). It is preferred particularly to react the compound (43) in a refluxing ethanol in the presence of triethylamine for 24 to 48 hours.

The compound (44) is hydrolyzed by a method known per se which has no effect on $P^1$, thereby obtaining a compound (45). It is preferred particularly to react the compound (44) in methanol in the presence of potassium hydroxide at room temperature to 60° C. for 1 to 3 hours.

The compound (45) is reacted with one equivalent to excess amount of an acid chloride in hydrocarbons such as benzene and toluene, ethers such as dioxane and tetrahydrofuran, halogenated-hydrocarbons such as methylene chloride and 1,2-dichloroethane in the presence of a base such as triethylamine, N,N-diisopropylethylamine or pyridine if necessary using a catalyst such as 4-dimethylaminopyridine at a temperature from room temperature to the boiling point of the employed solvent for several hours to several days, thereby obtaining a compound (46). It is preferred particularly to effect the reaction using methylene chloride as a solvent in the presence of triethylamine using a catalytic amount of 4-dimethylaminopyridine at room temperature for 24 to 48 hours.

The compound (46) is deprotected by a method known per se to obtain a compound (2E). When $P^1$ is tert-butoxycarbonyl, it is preferred to react trifluoroacetic acid in methylene chloride at room temperature for 1 to 5 hours. When $P^1$ is benzyloxycarbonyl, it is preferred to effect hydrogenation in methanol in the presence of 5% palladium/carbon at room temperature under atmospheric pressure.

(f) When E is Ethynylene and X and Y are Both N in the Compoumd (2)

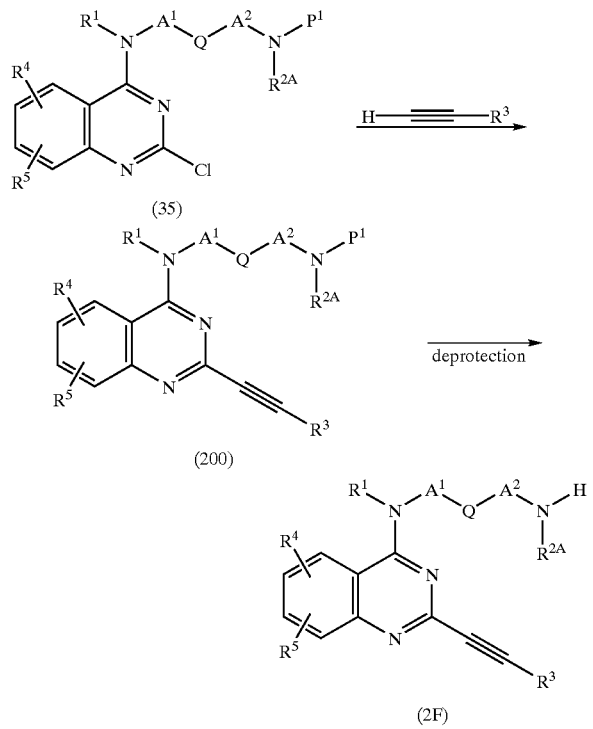

(wherein $R^1$, $R^{2A}$, $R^3$, $R^4$, $R^5$, $A^1$, $A^2$, Q and $P^1$ are the same meanings as described above.)

Starting from the compound (35), a known method (see Heterocycles 24, 2311 (1986) and the like) is employed to obtain a compound (200). The compound (200) is deprotected by a method known per se to obtain a compound (2F).

(g) When E is —CONR— and X and Y are Both N in the Compound (2)

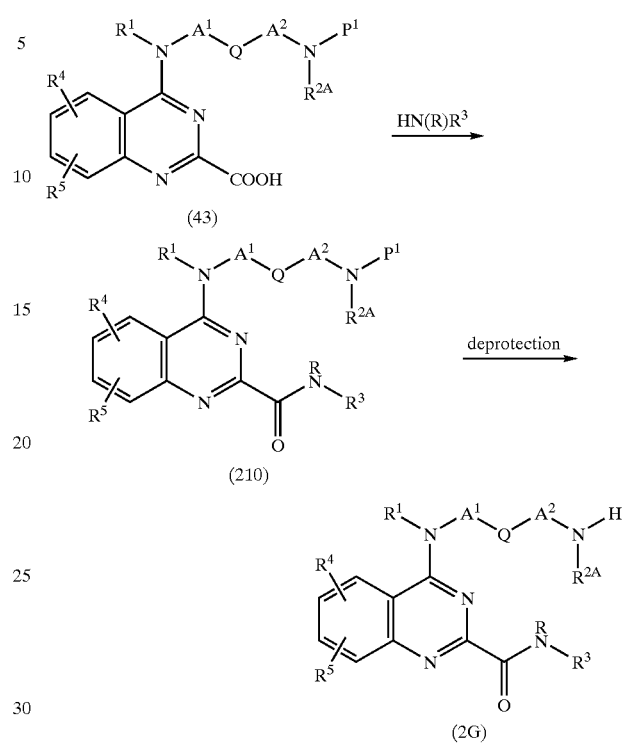

(wherein R, $R^1$, $R^{2A}$, $R^3$, $R^4$, $R^5$, $A^1$, $A^2$, Q and $P^1$ are the same meanings as described above.)

Starting from the compound (43), an amidation method known per se is employed to produce a compound (210). The compound (210) is then deprotected by a method per se to obtain a compound (2G).

(h) When E is —NRSO$_2$— and X and Y are Both N in the Compound (2)

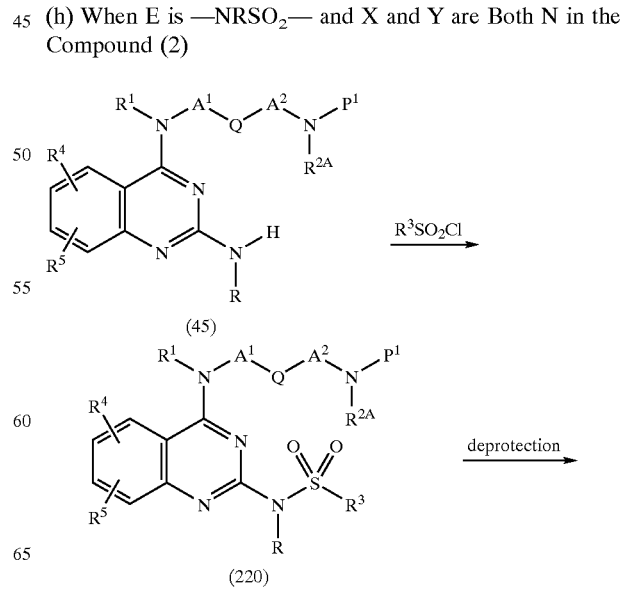

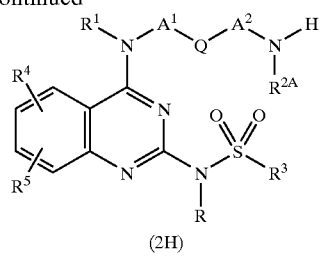

(2H)

(wherein R, R$^1$, R$^{2A}$, R$^3$, R$^4$, R$^5$, A$^1$, A$^2$, Q and P$^1$ are the same meanings as described above.)

Starting from the compound (45) and in accordance with a sulfonamidation method known per se, a compound (220) can be produced. The compound (220) is then deprotected by a method known per se to obtain a compound (2H).

(i) When E is —NRCONH— and X and Y are Both N in the Compound (2)

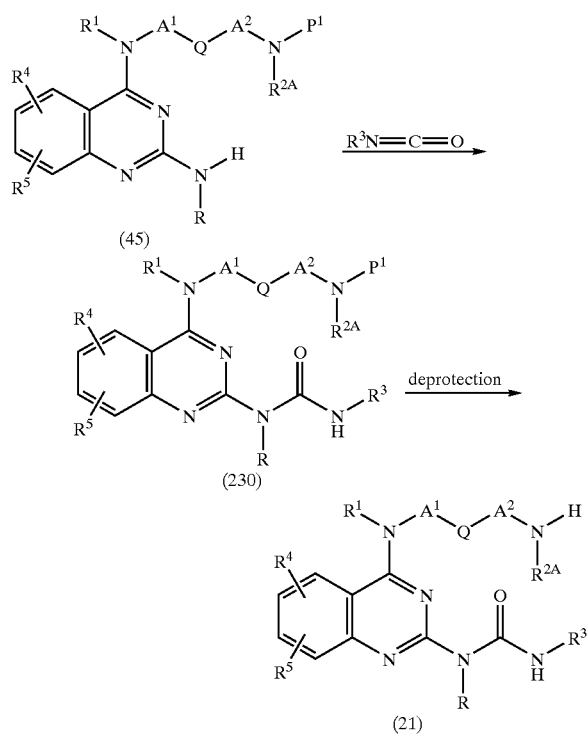

(wherein R, R$^1$, R$^{2A}$, R$^3$, R$^4$, R$^5$, A$^1$, A$^2$, Q and P$^1$ are the same meanings as described above.)

Starting from the compound (45), an isocyanate is reacted by a method known per se to produce a compound (230). The compound (230) is then deprotected by a method known per se to obtain a compound (2I).

A starting compound (3) can be produced in accordance with a known method (J. Org. Chem. 34, 616, 1969; Synthesis 6, 460, 1988 and the like).

A starting compound (4) can be produced in accordance with the following reaction scheme.

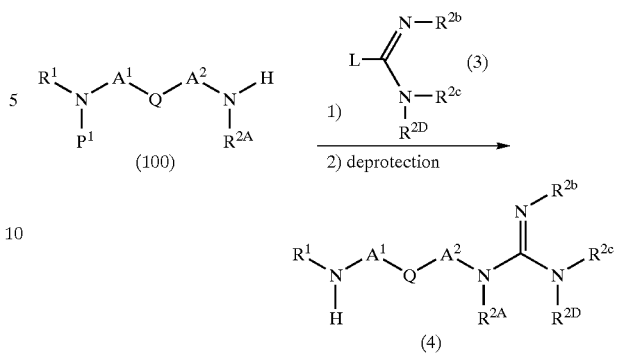

(wherein R$^1$, R$^{2A}$, R$^{2b}$, R$^{2c}$, R$^{2D}$, A$^1$, A$^2$, Q, L and P$^1$ are the same meanings as described above.)

The compound (100) is reacted similarly to Production Method A described above to obtain the starting compound (4). This starting compound (100) may be commercially available or can be produced by a method known per se.

A starting compound (120) can be produced in accordance with the following reaction scheme.

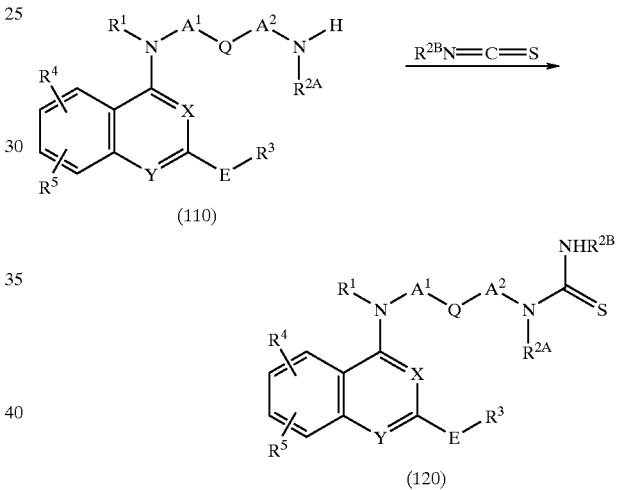

(wherein R$^1$, R$^{2A}$, R$^{2B}$, R$^3$, R$^4$, R$^5$, A$^1$, A$^2$, E, Q, X and Y are the same meanings as described above.)

A compound (110) is reacted with one equivalent to excess amount of R$^{2B}$N=C=S in a solvent similar to that in Production Method A described above if necessary in the presence of a base such as triethylamine or N,N-diisopropylethylamine at a temperature from room temperature to the boiling point of the employed solvent for several hours to several days to obtain the starting compound (120). It is preferred particularly to react in methylene chloride at room temperature for 1 to 24 hours.

In a production method described above, an amino group or hydroxyl group may be protected if necessary by a protective group employed conventionally, and after being subjected to the reaction it can be deprotected at an appropriate stage by a method known per se such as treatment with an acid or alkali or by catalytic hydrogenation. Examples of an amino protective group may include benzyl, benzyloxycarbonyl, t-butoxycarbonyl and trifluoroacetyl. Examples of a hydroxyl protective group may include methoxymethyl, 2-methoxyethoxymethyl, methylthiomethyl, tetrahydropyranyl, tert-butyl, benzyl, trimethylsilyl, tert-butyldimethylsilyl and the like.

A salt of the compound (1) of the present invention can be produced by a method known per se. For example, a hydrochloride of the compound (1) of the present invention can be obtained by treating the compound (1) of the present invention with a solution of hydrogen chloride in an alcohol or ethyl ether followed by recovering the precipitated crystals by filtration, or, in case where no crystal is precipitated, by concentrating the solution to precipitate crystals which are then recovered by filtration.

Since a compound according to the present invention represented by the formula (1) binds to a nociceptin receptor as shown in Test Examples described later to exert an agonist or antagonistic effect, it is useful as an analgesic, anti-inflammatory agent, diuretic, anesthetic, anti-hypertensive agent, anti-anxiety agent, anti-obesity agent, auditory controller, anti-depressant, anti-dementia agent, narcotic analgesic resistance-overcoming agent.

When an compound of the present invention is administered as a medicament, it can be administered to a mammal including human as it is or in a mixture with a pharmaceutically acceptable non-toxic inert carrier, for example, as a pharmaceutical composition containing the compound at a level of 0.1% to 99.5%, preferably 0.5% to 90%.

As a carrier, one or more of auxiliary agents for a formulation such as solid, semi-solid and liquid diluent, filler and other auxiliary agents for a drug formulation may be used. It is desirable that a pharmaceutical composition is administered as a unit dosage form. Since a compound of the present invention is water-soluble, it can be employed not only in a solid formulation but also in a liquid formulation (e.g., intravenous injection formulation, bladder infusion, oral syrup). The pharmaceutical composition can be administered into tissue, or orally, topically (percutaneously) or rectally. It is a matter of course that a dosage form suitable for any of the administration modes described above is employed. For example, oral or intravenous administration is preferable.

While it is desirable that the dose as an analgesic may be adjusted depending on the conditions of the patients including the age, body weight, nature and degree of the pain as well as the administration route, a daily dose as an active ingredient in an adult is usually 1 mg to 1000 mg per adult, preferably 1 mg to 500 mg per adult when given orally, and usually 1 mg to 100 mg per adult, preferably 1 mg to 50 mg per adult when given intravenously. In some cases, a lower dose may be sufficient or a higher dose may be required. Usually, the dose is given once or several times as being divided into portions, or given intravenously and continuously over a period of 1 to 24 hours a day.

The administration into a tissue can be accomplished by using a liquid unit dosage form, for example in the form of a solution or suspension, of a subcutaneous, intramuscular, bladder or intravenous injection formulation. Any of these formulations can be produced by suspending or dissolving a certain amount of a compound in a non-toxic liquid carrier such as an aqueous or oily medium compatible with the purpose of the injection followed by sterilizing said suspension or solution. Alternatively, a certain amount of a compound is placed in a vial, which is then sterilized together with its content and then sealed. For reconstitution or mixing just before use, a powdery or freeze-dried active ingredient is provided with a complementary vial or carrier. It is also possible to add a non-toxic salt or salt solution for the purpose of making an injection solution isotonic. It is also possible to use a stabilizer, preservative, emulsifier and the like.

Oral administration can be accomplished in a solid or liquid dosage form, such as a particle, powder, tablet, sugar-coated tablet, capsule, granule, suspension, liquid, syrup, drop, buccal formulation, suppository or other dosage forms. A particle is produced by pulverizing an active ingredient into a suitable particle size. A powder can be produced by pulverizing an active ingredient into a suitable particle size followed by mixing with a pharmaceutical carrier, such as an edible carbohydrate including starches or mannitol, which has also been pulverized into a suitable particle size. Those which may be added if necessary are flavors, preservatives, dispersing agents, colorants, fragrances and the like.

A capsule may be produced by filling a particle or powder which has previously been pulverized as described above or a granule obtained as described in the section of a tablet for example in a capsule such as a gelatin capsule. It is also possible that an additive such as a lubricant, fluidizing agent, such as colloidal silica, talc, magnesium stearate, calcium stearate or solid polyethylene glycol is mixed with the pulverized material prior to the filling procedure. For the purpose of enhancing the availability of a medicament when a capsule is ingested, a disintegrant or solubilizing agent, such as carboxymethyl cellulose, calcium carboxymethyl cellulose, low substituted hydroxypropyl cellulose, sodium croscarmellose, sodium carboxy starch, calcium carbonate or sodium carbonate, may be added.

The finely pulverized powder may be suspended and dispersed in a vegetable oil, polyethylene glycol, glycerin and surfactant, and then encapsulated in a gelatin sheet, thereby obtaining a soft capsule. A tablet is produced by formulating a powder mix, converting into a granule or slug, adding a disintegrant or lubricant and then compacting into a tablet. The powder mix is obtained by mixing an appropriately pulverized material with a diluent or base described above if necessary together with a binder (for example, sodium carboxymethyl cellulose, hydroxypropyl cellulose, methyl cellulose, hydroxypropylmethyl cellulose, gelatin, polyvinyl pyrrolidone, polyvinyl alcohol and the like), a dissolution retardant (for example, paraffin, wax, hardened castor oil and the like), a resorption promoter (for example, quaternary salt), or an adsorbent (for example, bentonite, kaolin, calcium diphosphate and the like). The powder mix can be granulated by wetting with a binder such as a syrup, starch glue, gum arabic, cellulose solution or polymer solution and then forcing to pass through a sieve. Instead of the procedure for granulating a powder as described above, another procedure may be employed in which a mix is subjected first to a tablet compacting machine to form a morphologically incomplete slug which is then ground.

A granule thus obtained may contain, as a lubricant, stearic acid, stearates, talc, mineral oil and the like, for the purpose of preventing any adhesion with each other. The mixture thus lubricated is then compacted into tablets.

A plane tablet thus obtained may be film-coated or sugar-coated.

An active ingredient may be mixed with a fluidized inert carrier and then compacted directly into tablets without being subjected to the granulating or slugging process described above. A transparent or semi-transparent protective film in the form of a shellac sealing film, a film of a sugar or polymeric material and a glossy film of a wax may also be employed.

Other oral dosage forms, such as a solution, syrup and elixir can be formulated as a unit dosage form whose certain amount contains a certain amount of a medicament. A syrup is produced by dissolving a compound in a flavored aqueous solution, while an elixir is produced by using a non-toxic alcoholic carrier. A suspension is formulated by dispersing a compound in a non-toxic carrier. Additives such as a solubilizing agent, an emulsifier (for example ethoxylated isostearyl alcohols, polyoxyethylene sorbitol esters), a preservative and a flavor (for example, peppermint oil, saccharin) may also be added if necessary.

An oral unit dosage formulation may also be a microcapsule if desired. Such a formulation may be coated or embedded in a polymer or wax to obtain a prolonged activity or sustained release of the active ingredient.

A rectal administration can be accomplished by using a suppository obtained by mixing a compound with a water-soluble or water-insoluble solid having a low melting point such as a polyethylene glycol, cocoa butter, higher esters (for example, myristyl palmitate) as well as a mixture thereof.

BEST MODE FOR CARRYING OUT THE INVENTION

Next, the present invention will be described in more detail with reference to a production examples of typical starting materials (Reference Examples), production examples of a compound according to the present invention (Examples), formulation examples and test examples, which is not limited thereto. Noted that an optical rotation was measured at 20° C.

REFERENCE EXAMPLE 1
N-tert-Butoxycarbonyl-1,6-hexanediamine

A solution of 5.9 g of 1,6-hexanediamine in 30 mL of tetrahydrofuran was combined with 30 mL of a 2% aqueous solution of sodium hydroxide, and cooled to 0° C. This was treated dropwise with a solution of 4.46 g of di-tert-butyl dicarbonate in 30 mL of tetrahydrofuran, and stirred for 15 hours while gradually warming to room temperature. The reaction solution was combined with water, extracted with ethyl acetate, dried over sodium sulfate, and then concentrated. The residue was purified by chromatography on silica gel to obtain 3.1 g of the desirable compound.

The following compounds were produced by the method similar to that in Reference Example 1.

N-tert-Butoxycarbonyl-1,2-ethylenediamine
N-tert-Butoxycarbonyl-1,3-propanediamine
N-tert-Butoxycarbonyl-1,4-butanediamine
N-tert-Butoxycarbonyl-1,5-pentanediamine
N-tert-Butoxycarbonyl-1,7-heptanediamine
N-tert-Butoxycarbonyl-1,8-octanediamine
N-tert-Butoxycarbonylpiperazine
cis-N-tert-Butoxycarbonyl-1,2-cyclohexanediamine
trans-N-tert-Butoxycarbonyl-1,2-cyclohexanediamine
cis-N-tert-Butoxycarbonyl-1,3-cyclohexanediamine
trans-N-tert-Butoxycarbonyl-1,3-cyclohexanediamine
cis-N-tert-Butoxycarbonyl-1,4-cyclohexanediamine
trans-N-tert-Butoxycarbonyl-1,4-cyclohexanediamine

REFERENCE EXAMPLE 2
(1S,2R)-2-tert-Butoxycarbonylamino-cyclohexylamine
Step 1
(1R,2R)-N-tert-Butoxycarbonyl-2-benzyloxycyclohexylamine A solution of 3.0 g of (1R,2R)-2-benzyloxycyclohexylamine in 30 mL of tetrahydrofuran was combined with 30 mL of a 2% aqueous solution of sodium hydroxide, and cooled to 0° C. This was treated dropwise with a solution of 4.46 g of di-tert-butyl dicarbonate in 30 mL of tetrahydrofuran, and stirred for 15 hours while gradually warming to room temperature. The reaction solution was combined with water, and extracted with ethyl acetate. After drying over magnesium sulfate, 4.45 g of the desirable compound was obtained by concentration.

Step 2
(1R, 2R)-N-tert-Butoxycarbonyl-2-hydroxycyclohexylamine

A solution of 3.0 g of (1R,2R)-N-tert-butoxycarbonyl-2-benzyloxycyclohexylamine in 100 mL of methanol was combined with 300 mg of 5% palladium on carbon, and hydrogenated at room temperature under atmospheric pressure. After 48 hours, palladium on carbon was filtered off, and the filtrate was concentrated. The residue was subjected to chromatography on silica gel (n-hexane:ethyl acetate 2:1) to obtain 2.0 g of the desirable compound.

Step 3
(1R,2S)-N-tert-Butoxycarbonyl-2-phthaliminocyclohexylamine

Under argon atmosphere, a solution of 500 mg of (1R, 2R)-N-tert-butoxycarbonyl-2-hydroxycyclohexylamine in 20 mL of anhydrous tetrahydrofuran was combined with 913 mg of triphenylphosphine and 513 mg of phthalimide, treated dropwise with 1.58 mL of a 40% solution of azodicarboxylic acid diethyl ester in toluene with cooling in ice, and stirred for 24 hours while allowing to gradually warm to room temperature. After solvent was distilled off, the residue was purified by column chromatography on silica gel (n-hexane:ethyl acetate 2:1) to obtain 550 mg of the desirable compound.

Step 4
(1S,2R)-2-tert-Butoxycarbonylaminocyclohexylamine

A solution of 2.50 g of (1R,2S)-N-tert-butoxycarbonyl-2-phthaliminocyclohexylamine in 80 mL of ethanol was combined with 1.82 g of hydrazine hydrate, and refluxed for 3 hours. After the solvent was distilled off, the residue was combined with a 10% aqueous solution of sodium hydroxide, and extracted with chloroform. After concentrating, the residue was purified by column chromatography on silica gel (chloroform:methanol=10:1) to obtain 1.60 g of the desirable compound.

The following compounds were produced by the method similar to that in Reference Example 2.

(1R,2S)-2-tert-Butoxycarbonylaminocyclohexylamine
(1R,2S)-2-tert-Butoxycarbonylaminocyclopentylamine
(1S,2R)-2-tert-Butoxycarbonylaminocyclopentylamine
4-Amino-N-tert-butoxycarbonylpiperidine

REFERENCE EXAMPLE 3
1-tert-Butoxycarbonylamino-6-aminoheptane
Step 1
6-tert-Butoxycarbonylamino-1-hexanol A solution of 5.1 g of 6-amino-1-hexanol in 100 mL of chloroform was treated dropwise with 10.4 g of di-tert-butyl dicarbonate, and stirred for 12 hours. The reaction solution was concentrated, and the residue was washed with n-hexane to obtain 9.40 g of the desirable compound as white crystals.

Step 2
6-tert-Butoxycarbonylaminohexanal

A solution of 1.0 g of 6-tert-butoxycarbonylamino-1-hexanol in 20 mL of methylene chloride was combined with 3 g of a 4 angstrom molecular sieve, 808 mg of N-methylmorpholine-N-oxide and a catalytic amount of tetrapropylammonium perruthenate, and stirred for 24 hours. The reaction solution was filtered through Celite, and concentrated. The residue was purified by column chromatography on silica gel (n-hexane:ethyl acetate=2:1) to obtain 660 mg of the desirable compound.

Step 3
1-tert-Butoxycarbonylamino-6-hydroxyheptane

Under argon atmosphere, a solution of 650 mg of 6-tert-butoxycarbonylaminohexanal in 10 mL of anhydrous tetrahydrofuran was cooled to −78° C., and treated dropwise with 6.8 mL of methylmagnesium bromide (a 1.0 M solution in tetrahydrofuran). After 2 hours, the reaction solution was combined with water, extracted with ethyl acetate, and dried. After concentrating, the residue was purified by column chromatography on silica gel (n-hexane:ethyl acetate=2:1) to obtain 280 mg of the desirable compound.

Step 4
1-tert-Butoxycarbonylamino-6-phthaliminoheptane

Under argon atmosphere, a solution of 270 mg of 1-tert-butoxycarbonylamino-6-hydroxyheptane in 7 mL of anhydrous tetrahydrofuran was combined with 367 mg of triphenylphosphine and 258 mg of phthalimide, treated dropwise with 0.80 mL of a 40% solution of azodicarboxylic acid diethyl ester in toluene with cooling in ice, and stirred for 24 hours while allowing to gradually warm to room temperature. After the solvent was distilled off, the residue was purified by column chromatography on silica gel (n-hexane:ethyl acetate=4:1) to obtain 321 mg of the desirable compound.

Step 5
1-tert-Butoxycarbonylamino-6-aminoheptane

A solution of 321 mg of 1-tert-butoxycarbonylamino-6-phthaliminoheptane in 10 mL of ethanol was combined with 89 mg of hydrazine hydrate, and heated under reflux for 4 hours. After the solvent was distilled off, the residue was combined with a 10% aqueous solution of sodium hydroxide, and extracted with chloroform. After drying over sodium sulfate followed by concentrating, the residue was purified by column chromatography on silica gel (chloroform:methanol=10:1) to obtain 202 mg of the desirable compound.

REFERENCE EXAMPLE 4
cis-4-Trifluoroacetylaminomethylcyclohexylamine
Step 1
cis-4-Aminocyclohexanecarboxylic Acid Methyl Ester Hydrochloride A solution of 2.0 g of cis-4-aminocyclohexanecarboxylic acid in 20 mL of methanol was combined with 3.57 mL of thionyl chloride, and stirred for 3 hours. The reaction solution was concentrated, and the residue was washed with ethyl ether to obtain 2.64 g of the desirable compound as colorless crystals.

Step 2
cis-4-(tert-Butoxycarbonylamino)cyclohexanecarboxylic Acid Methyl Ester

A solution of 2.64 g of cis-4-aminocyclohexanecarboxylic acid methyl ester hydrochloride in 30 mL of chloroform was combined with 1.52 g of triethylamine, and 3.27 g of di-tert-butyl dicarbonate was added dropwise to this. After 3 hours, the reaction solution was combined with water, extracted with chloroform, and then dried over magnesium sulfate. The solvent was distilled off, and the residue was purified by column chromatography on silica gel (chloroform) to obtain 3.62 g of the desirable compound.

Step 3
cis-N-(tert-Butoxycarbonyl)-4-hydroxymethylcyclohexylamine

Under argon atmosphere, a suspension of 1.29 g of lithium aluminum hydride in 40 mL of anhydrous ethyl ether was treated dropwise with a solution of 5.80 g of cis-4-(tert-butoxycarbonylamino)cyclohexanecarboxylic acid methyl ester in 20 mL of anhydrous ethyl ether with cooling in ice, and stirred for 3 hours while allowing to gradually warm to room temperature. The reaction solution was cooled to 0° C., combined a small amount of water to decompose an excessive lithium aluminum hydride. The insolubles were filtered off through Celite, and the filtrate was concentrated, and then the residue was washed with n-hexane to obtain 3.60 g of the desirable compound as colorless crystals.

Step 4
cis-N-(tert-Butoxycarbonyl)-4-phthaliminomethylcyclohexylamine

Under argon atmosphere, a solution of 3.60 g of cis-N-(tert-butoxycarbonyl)-4-hydroxymethylcyclohexylamine in 50 mL of anhydrous tetrahydrofuran was combined with 4.12 g of triphenylphosphine and 2.31 g of phthalimide, treated dropwise with 6.84 mL of a 40% solution of azodicarboxylic acid diethyl ester in toluene with cooling in ice, and stirred for 15 hours while allowing to gradually warm to room temperature. The solvent was distilled off, and the residue was purified by column chromatography on silica gel (chloroform) to obtain 3.45 g of the desirable compound.

Step 5
cis-N-(tert-Butoxycarbonyl)-4-trifluoroacetylaminomethylcyclohexylamine

A solution of 3.45 g of cis-N-(tert-butoxycarbonyl)-4-phthaliminomethylcyclohexylamine in 35 mL of ethanol was combined with 0.72 g of hydrazine hydrate, and heated under reflux for 5 hours. The solvent was distilled off, and the residue was combined with a 10% aqueous solution of sodium hydroxide, and extracted with chloroform. After concentrating, a solution of the residue in 25 mL of methanol was combined with 1.17 g of triethylamine and 1.64 g of trifluoroacetic acid ethyl ester, and stirred for 15 hours. After the reaction solution was concentrated, the residue was purified by column chromatography on silica gel (chloroform:methanol=40:1) to obtain 2.50 g of the desirable compound.

Step 6
cis-4-Trifluoroacetylaminomethylcyclohexylamine

A solution of 0.53 g of cis-N-(tert-butoxycarbonyl)-4-trifluoroacetylaminomethylcyclohexylamine in methylene chloride was combined with 2 mL of trifluoroacetic acid, and stirred for 2 hours. The reaction solution was basified by addition of a saturated solution of sodium hydrogen carbonate, and then extracted with chloroform. After drying over sodium sulfate, 0.19 g of the desirable compound was obtained as a pale yellow oil.

The following compound was produced by the method similar to that in Reference Example 4.
cis-2-Trifluoroacetylaminomethylcyclohexylamine REFERENCE EXAMPLE 5
trans-N-tert-Butoxycarbonyl-1,4-bis(aminomethyl)cyclohexane
Step 1
trans-1,4-Cyclohexanedicarboxylic Acid Dimethyl Ester With cooling in ice, 25 mL of methanol was treated dropwise with 6 mL of thionyl chloride, and stirred for 1 hour. This was combined with 3.44 g of trans-1,4-cyclohexanedicarboxylic acid, and stirred at room temperature for 20 hours. After the reaction solution was concentrated, the residue was combined with ice, and basified by addition of a 10% aqueous solution of sodium hydroxide. The mixture was extracted with chloroform, dried, and then concentrated. The residue was washed with n-hexane to obtain 3.9 g of the desirable compound.

Step 2
trans-1,4-Bis(hydroxymethyl)cyclohexane

Under argon stream, a suspension of 2.96 g of lithium aluminum hydride in 100 mL of anhydrous tetrahydrofuran was treated dropwise with a solution of 3.9 g of trans-1,4-cyclohexanedicarboxylic acid dimethyl ester in anhydrous tetrahydrofuran at −20° C., and stirred for 2.5 hours. The reaction solution was combined with ice water to complete the reaction, and the insolubles were filtered off through Celite. After drying over magnesium sulfate, the residue was concentrated to obtain 2.80 g of the desirable compound.
Step 3
trans-1,4-Bis(phthaliminomethyl)cyclohexane A solution of 1.60 g of trans-1,4-bis(hydroxymethyl)cyclohexane in 200 mL of toluene was combined with 6.98 g of triphenylphosphine, treated dropwise with 3.92 g of phthalimide and 11.58 mL of a 40% solution of azodicarboxylic acid diethyl ester in toluene with cooling in ice, and stirred for 18 hours. The residue was combined with water, extracted with chloroform, dried, and then concentrated. The residue was washed with ethyl ether and methanol to obtain 3.53 g of the desirable compound.
Step 4
trans-N,N'-Di-tert-butoxycarbonyl-1,4-bis(aminomethyl)cyclohexane A suspension of 3.50 g of trans-1,4-bis(phthaliminomethyl)cyclohexane in 50 mL of ethanol was combined with 4.35 g of hydrazine hydrate, and heated under reflux for 2 hours. The reaction solution was concentrated, combined with 20 mL of a 10% aqueous solution of sodium hydroxide and 30 mL of 1,4-dioxane, treated dropwise with 6.50 g of di-tert-butyl dicarbonate with cooling in ice, and then stirred at room temperature for 2 hours. After extracting with chloroform, the extract was dried and concentrated. The residue was washed with n-hexane, and dried to obtain 2.80 g of the desirable compound.
Step 5
trans-N-tert-Butoxycarbonylbis-1,4-(aminomethyl)cyclohexane A solution of 2.75 g of trans-N,N'-di-tert-butoxycarbonyl-1,4-bis(aminomethyl)cyclohexane in 40 mL of methylene chloride was combined with 5 mL of 4 N solution of hydrogen chloride in ethyl acetate, and stirred at room temperature for 2 hours, and then the reaction solution was concentrated. This was combined with 40 mL of a 10% aqueous solution of sodium hydroxide and 20 mL of 1,4-dioxane, treated dropwise with 0.90 g of di-tert-butyl dicarbonate with cooling in ice, and stirred at room temperature for 2 hours. After extracting with chloroform, the extract was dried and concentrated. The residue was purified by column chromatography on silica gel (chloroform:methanol=20:1) to obtain 0.25 g of the desirable compound.

The following compound was produced by the method similar to that in Reference Example 5.
cis-N-tert-Butoxycarbonyl-1,4-bis(aminomethyl)cyclohexane

EXAMPLE 1
cis-N-Amidino-2-[2-(4-chlorostyryl)-6-methoxyquinazolin-4-yl]aminocyclohexylamine Dihydrochloride
Step 1
cis-N-tert-Butoxycarbonyl-2-[2-(4-chlorostyryl)-6-methoxyquinazolin-4-yl]aminocyclohexylamine A solution of 391 mg of 4-chloro-2-(4-chlorostyryl)-6-methoxyquinazoline, 379 mg of cis-2-(tert-butoxycarbonyl)aminocyclohexylamine, and 358 mg of triethylamine in 20 mL of toluene was combined with a catalytic amount of 4-dimethylaminopyridine, and heated under reflux for 20 hours. After distilling the reaction solution off, the residue was combined with water, extracted with chloroform, dried over magnesium sulfate, and concentrated. The residue was purified by column chromatography on silica gel (chloroform:methanol=50:1) to obtain 580 mg of the desirable compound.
Step 2
cis-2-[2-(4-Chlorostyryl)-6-methoxyquinazolin-4-yl]aminocyclohexylamine A solution of 520 mg of cis-N-tert-butoxycarbonyl-2-[2-(4-chlorostyryl)-6-methoxyquinazolin-4-yl]aminocyclohexylamine in 10 mL of methanol was combined with 5 mL of a 4 N solution of hydrogen chloride in ethyl acetate, and reacted at 50° C. for 24 hours. After the solvent was distilled off, the residue was basified by addition of a 10% aqueous solution of sodium hydroxide, and extracted with chloroform. After concentrating, the residue was purified by column chromatography on silica gel (chloroform:methanol=10:1) to obtain 378 mg of the desirable compound.
Step 3
cis-N-[N,N'-Bis(tert-butoxycarbonyl)]amidino-2-[2-(4-chlorostyryl)-6-methoxyquinazolin-4-yl]aminocyclohexylamine A solution of 400 mg of cis-2-[2-(4-chlorostyryl)-6-methoxyquinazolin-4-yl]aminocyclohexylamine in 5 mL of dichloroethane and 1 mL of N,N-dimethylformamide was combined with 273 mg of N,N'-bis(tert-butoxycarbonyl)-1H-pyrazole-1-carboxyamidine, and stirred at room temperature for 15 hours. The reaction solution was combined with water, and extracted with ethyl acetate. The organic layer was then washed with water and saturated brine, and dried over magnesium sulfate. After concentrating, the residue was purified by column chromatography on silica gel (chloroform:methanol=30:1) to obtain 580 mg of the desirable compound.
Step 4
cis-N-Amidino-2-[2-(4-chlorostyryl)-6-methoxyquinazolin-4-yl]aminocyclohexylamine Dihydrochloride A solution of 570 mg of cis-N-[N,N'-bis(tert-butoxycarbonyl)]amidino-2-[2-(4-chlorostyryl)-6-methoxyquinazolin-4-yl]aminocyclohexylamine in 8 mL of methanol and 8 mL of chloroform was combined with 5 mL of a 4N solution of hydrogen chloride in ethyl acetate, and reacted at 50° C. for 48 hours. After concentrating, crystallization are performed with ethyl acetate to obtain 310 mg of the desirable compound as pale yellow crystals.

Cation FAB-MS m/z: 451[M+H]$^+$

Element analytical value (as $C_{24}H_{27}N_6ClO \cdot 2HCl \cdot 2H_2O$) Calculated value (%) C: 51.48; H: 5.94; N: 15.01. Found value (%) C: 51.75; H: 5.64; N: 15.01.

EXAMPLE 2
cis-N-Amidino-2-[2-(4-chlorobenzoylamino)-6-methoxyquinazolin-4-yl]aminocyclohexylamine Dihydrochloride
Step 1
cis-N-tert-Butoxycarbonyl-2-(2-ethoxycarbonyl-6-methoxyquinazolin-4-yl)aminocyclohexylamine A solution of 1.96 g of 4-chloro-2-ethoxycarbonyl-6-methoxyquinazoline in 70 mL of toluene was combined with 1.58 g of cis-2-tert-butoxycarbonylaminocyclohexylamine and 0.74 g of triethylamine, and heated under reflux for 15 hours. After concentrating, the mixture was combined with water, extracted with chloroform, and dried. After the solvent was distilled off, the residue was purified by column chromatography on silica gel (chloroform) to obtain 2.70 g of the desirable compound.

Step 2
cis-N-tert-Butoxycarbonyl-2-(2-carboxy-6-methoxyquinazolin-4-yl)aminocyclohexylamine A solution of 1.70 g of cis-N-tert-butoxycarbonyl-2-(2-ethoxycarbonyl-6-methoxyquinazolin-4-yl)aminocyclohexylamine in 5 mL of methanol was combined with 5 mL of a 1N aqueous solution of sodium hydroxide, and stirred at room temperature for 3 hours. After the pH was adjusted to 5 by addition of a 1N aqueous solution of potassium hydrogen sulfate to the reaction solution, which was then extracted with chloroform and dried. After the solvent was distilled off, the residue was purified by column chromatography on silica gel (chloroform:methanol=10:1) to obtain 1.10 g of the desirable compound.

Step 3
cis-N-tert-Butoxycarbonyl-2-(2-ethoxycarbonylamino-6-methoxyquinazolin-4-yl)aminocyclohexylamine A solution of 1.03 g of cis-N-tert-butoxycarbonyl-2-(2-carboxy-6-methoxyquinazolin-4-yl)aminocyclohexylamine in 10 mL of tetrahydrofuran was combined with 0.82 g of diphenylphosphoryl azide, 1.14 g of ethanol and 0.3 g of triethylamine, and reacted at 80° C. for 72 hours. The reaction solution was concentrated, and then combined with water, extracted with chloroform, and dried. After the solvent was distilled off, the residue was purified by column chromatography on silica gel (chloroform:methanol=50:1) to obtain 800 mg of the desirable compound.

Step 4
cis-2-(2-Amino-6-methoxyquinazolin-4-yl)amino-N-tert-butoxycarbonylcyclohexylamine A solution of 300 mg of cis-N-tert-butoxycarbonyl-2-(2-ethoxycarbonylamino-6-methoxyquinazolin-4-yl)aminocyclohexylamine in 10 mL of methanol was combined with a 50 mg of potassium hydroxide powder, and stirred at room temperature for 3 hours. The reaction solution was neutralized by addition of a saturated aqueous solution of ammonium chloride, and then extracted with chloroform and dried. After the solvent was distilled off, the residue was purified by column chromatography on silica gel (chloroform:methanol=10:1) to obtain 250 mg of the desirable compound.

Step 5
cis-N-tert-Butoxycarbonyl-2-[2-(4-chlorobenzoylamino)-6-methoxyquinazolin-4-yl]aminocyclohexylamine A solution of 68 mg of 4-chlorobenzoyl chloride and 200 mg of diisopropylethylamine in 8 mL of methylene chloride was combined with 150 mg of cis-2-(2-amino-6-methoxyquinazolin-4-yl)amino-N-tert-butoxycarbonylcyclohexylamine, and stirred at room temperature for 15 hours. The reaction solution was combined with water, extracted with chloroform, and dried. After the solvent was distilled off, the residue was purified by column chromatography on silica gel (chloroform:methanol=30:1) to obtain 120 mg of the desirable compound.

Step 6
cis-2-[2-(4-Chlorobenzoylamino)-6-methoxyquinazolin-4-yl]aminocyclohexylamine A solution of 120 mg of cis-N-tert-butoxycarbonyl-2-[2-(4-chlorobenzoylamino)-6-methoxyquinazolin-4-yl]aminocyclohexylamine in 5 mL of methylene chloride was combined with 2 mL of trifluoroacetic acid, and reacted at room temperature for 1 hour. The reaction solution was basified by addition of a saturated solution of sodium hydrogen carbonate, extracted with chloroform, and dried. After the solvent was distilled off, the residue was purified by column chromatography on silica gel (chloroform:methanol=30:1) to obtain 80 mg of the desirable compound.

Step 7
cis-N-[N,N'-Bis(tert-butoxycarbonyl)]amidino-2-[2-(4-chlorobenzoylamino)-6-methoxyquinazolin-4-yl]aminocyclohexylamine A solution of 80 mg of cis-2-[2-(4-chlorobenzoylamino)-6-methoxyquinazolin-4-yl]aminocyclohexylamine in 5 mL of dichloroethane and 1 mL of N,N-dimethylformamide was combined with 58 mg of N,N'-bis(tert-butoxycarbonyl)-1H-pyrazole-1-carboxyamidine, and stirred at room temperature for 15 hours. The reaction solution was combined with water, and extracted with ethyl acetate. The organic layer was washed with water and saturated brine, and then dried over magnesium sulfate. After concentrating, the residue was purified by column chromatography on silica gel (chloroform:methanol=30:1) to obtain 120 mg of the desirable compound.

Step 8
cis-N-Amidino-2-[2-(4-chlorobenzoylamino)-6-methoxyquinazolin-4-yl]aminocyclohexylamine Dihydrochloride A solution of 120 mg of cis-N-[N,N'-bis(tert-butoxycarbonyl)]amidino-2-[2-(4-chlorobenzoylamino)-6-methoxyquinazolin-4-yl]aminocyclohexylamine in 5 mL of methanol and 5 mL of chloroform was combined with 3 mL of a 4N solution of hydrogen chloride in ethyl acetate, and reacted at 50° C. for 72 hours. After concentrating, treatment was performed with methanol-ethyl ether to obtain 22 mg of the desirable compound as pale yellow powder.

Cation FAB-MS m/z: 468[M+H]$^+$

Element analytical value (as $C_{23}H_{26}ClN_7O_2 \cdot 2HCl \cdot 3H_2O$) Calculated value (%) C: 46.43; H: 5.76; N: 16.48. Found value (%) C: 46.45; H: 5.55; N: 16.25.

EXAMPLE 3 cis-N-Acetimide-2-[2-(4-chlorostyryl)-6-methoxyquinazolin-4-yl]aminocyclohexylamine Dihydrochloride A solution of 50 mg of cis-2-[2-(4-chlorostyryl)-6-methoxyquinazolin-4-yl]aminocyclohexylamine in 8 mL of ethanol was combined with 76 mg of ethylacetimidate and 123 mg of triethylamine, and heated under reflux for 3 hours. After the reaction solution was concentrated, the residue was purified by column chromatography on silica gel (chloroform:methanol:aqueous ammonia=100:10:1). A solution of 50 mg of the resultant cis-N-acetimide-2-[2-(4-chlorostyryl)-6-methoxyquinazolin-4-yl]aminocyclohexylamine in 3 mL of methanol was combined with 1 mL of a 4N solution of hydrochloric acid in ethyl acetate, and stirred at 30 minutes. After concentrating, crystallization was performed with ethyl ether to obtain 45 mg of the desirable compound as pale yellow crystals.

Element analytical value (as $C_{25}H_{28}ClN_5O_2 \cdot HCl \cdot 1.5H_2O$)
Cation FAB-MS m/z: 450[M+H]$^+$ Calculated value (%) C: 65.28; H: 6.14; N: 12.18. Found value (%) C: 65.23; H: 5.92; N: 12.12.

EXAMPLE 4 cis-4-Guanidinomethyl-N-{2-[2-(2-pyridyl)ethenyl]-6-methoxyquinazolin-4-yl}cyclohexylamine Trihydrochloride Step 1
cis-4-Trifluoroacetylaminomethyl-N-{2-[2-(2-pyridyl)ethenyl]-6-methoxyquinazolin-4-yl}cyclohexylamine A solution of 140 mg of cis-4-trifluoroacetylaminomethylcyclohexylamine in 15 mL of toluene was combined with 180 mg of 4-chloro-6-methoxy-2-[2-(2-pyridyl)ethenyl] quinazoline, 500 mg of triethylamine and 20 mg of 4-dimethylaminopyridine, and heated under reflux for 15 hours. After the reaction solution was distilled off, the residue was combined with water, and extracted with chloroform. After drying over magnesium sulfate and concentrating, the residue was purified by column chromatography on silica gel (chloroform:methanol=30:1) to obtain 140 mg of the desirable compound.

Step 2
cis-4-Aminomethyl-N-{2-[2-(2-pyridyl)ethenyl]-6-methoxyquinazolin-4-yl}cyclohexylamine A solution of cis-4-trifluoroacetylaminomethyl-N-{2-[2-(2-pyridyl)ethenyl]-6-methoxyquinazolin-4-yl}cyclohexylamine in 45 mL of methanol and 5 mL of water was combined with 414 mg of potassium carbonate, and stirred at room temperature for 15 hours. The reaction solution was combined with water, extracted with chloroform, and then dried over sodium sulfate and concentrated. The residue was purified by column chromatography on silica gel (chloroform:methanol:aqueous ammonia=100:10:1) to obtain 120 mg of the desirable compound.

Step 3
cis-4-Guanidinomethyl-N-{2-[2-(2-pyridyl)ethenyl]-6-methoxyquinazolin-4-yl}cyclohexylamine Trihydrochloride A solution of 120 mg of cis-4-aminomethyl-N-{2-[2-(2-pyridyl)ethenyl]-6-methoxyquinazolin-4-yl}cyclohexylamine in 15 mL of dichloroethane and 3 mL of N,N-dimethylformamide was combined with 150 mg of N,N'-bis(tert-butoxycarbonyl)-1H-pyrazole-1-carboxyamidine, and stirred at room temperature for 15 hours. The reaction solution was combined with water, and extracted with ethyl acetate. The organic layer was washed with water and saturated brine, and then dried over magnesium sulfate. After concentrating, the residue was purified by column chromatography on silica gel (chloroform:methanol 30:1). This was dissolved in 3 mL of methanol, combined with 3 mL of a 4N solution of hydrogen chloride in ethyl acetate, and reacted at 50° C. for 24 hours. The reaction solution was concentrated, and then treated with methanol-ethyl ether to obtain 84 mg of the desirable compound.

Cation FAB-MS m/z: 416[M+H]$^+$
Appearance: yellow powder

EXAMPLE 5
N-2-(2-Imidazolinyl)-N'-[2-(4-chlorostyryl)-6-methylquinazolin-4-yl]-1,4-cyclohexanediamine Dihydrochloride 100 mg of N-[2-(4-chlorostyryl)-6-methylquinazolin-4-yl]-1,4-cyclohexanediamine in 10 mL of methanol was combined with 82 mg of 1-tert-butoxycarbonyl-2-methylthio-2-imidazoline, and heated under reflux for 10 hours. The reaction solution was concentrated, and the residue was purified by column chromatography on silica gel (chloroform:methanol=20:1), and this was combined with 7 mL of a 4N solution of hydrogen chloride in ethyl acetate, and reacted at 50° C. for 24 hours. After concentrating, treatment was performed with methanol-ethyl ether to obtain 80 mg of the desirable compound.

Appearance: white powder
Element analytical value (as $C_{26}H_{29}ClN_6 \cdot 3HCl \cdot 2.5H_2O$)
Calculated value (%) C: 50.75; H: 6.06; N: 13.66. Found value (%) C: 51.15; H: 5.70; N: 13.47.

The compounds of the following Examples 6 to 48, 52 to 59, 61, and 64 to 68 were produced by the method similar to that in Example 1.

EXAMPLE 6
N-Amidino-N'-[2-(4-chlorostyryl)quinazolin-4-yl]-1,4-butanediamine Dihydrochloride
Cation FAB-MS m/z: 395[M+H]$^+$
Appearance: pale yellow crystals

EXAMPLE 7
N-Amidino-N'-[2-(4-chlorostyryl)quinazolin-4-yl]-1,5-pentanediamine Dihydrochloride
Cation FAB-MS m/z: 409[M+H]$^+$
Appearance: pale yellow powder
Element analytical value (as $C_{22}H_{25}ClN_6 \cdot 2HCl \cdot 1.5H_2O$)
Calculated value (%) C: 51.93; H: 5.94; N: 16.52. Found value (%) C: 51.99; H: 5.76; N: 16.25.

EXAMPLE 8
N-Amidino-N'-[2-(4-chlorostyryl)-6-methylquinazolin-4-yl]-1,6-hexanediamine Dihydrochloride
Cation FAB-MS m/z: 437[M+H]$^+$
Appearance: white powder

EXAMPLE 9
N-Amidino-N'-[2-(4-chlorostyryl)quinazolin-4-yl]-1,3-propanediamine Dihydrochloride
Cation FAB-MS m/z: 381[M+H]$^+$
Appearance: pale red powder
Element analytical value (as $C_{20}H_{21}ClN_6 \cdot 2HCl \cdot H_2O$)
Calculated value (%) C: 50.91; H: 5.34; N: 17.82. Found value (%) C: 50.79; H: 5.07; N: 18.30.

EXAMPLE 10
N-Amidino-N'-[2-(4-chlorostyryl)-6-methylquinazolin-4-yl]-1,4-butanediamine Dihydrochloride
Cation FAB-MS m/z: 409[M+H]$^+$
Appearance: pale yellow powder

EXAMPLE 11
N-Amidino-N'-[2-(4-chlorostyryl)-6-methylquinazolin-4-yl]-1,5-pentanediamine Dihydrochloride
Cation FAB-MS m/z: 423[M+H]$^+$
Appearance: white powder

EXAMPLE 12
cis-N-Amidino-2-[2-(4-chlorostyryl)-6-methylquinazolin-4-yl]aminocyclohexylamine Dihydrochloride
Cation FAB-MS m/z: 435[M+H]$^+$
Appearance: yellow powder
Element analytical value (as $C_{24}H_{27}ClN_6 \cdot 3HCl$)
Calculated value (%) C: 52.96; H: 5.55; N: 15.44. Found value (%) C: 52.60; H: 5.73; N: 15.77.

EXAMPLE 13
(1R,2S)-N-Amidino-2-[2-(4-chlorostyryl)-6-methylquinazolin-4-yl]aminocyclohexylamine Dihydrochloride
Cation FAB-MS m/z: 435[M+H]$^+$
Element analytical value (as $C_{24}H_{27}ClN_6 \cdot HCl \cdot 2.5H_2O$)
Calculated value (%) C: 52.13; H: 6.20; N: 15.20. Found value (%) C: 52.40; H: 5.80; N: 15.43. Optical rotation $[\alpha]_D^{20}=+87.6°$ (c=1.0, methanol)

EXAMPLE 14
(1S,2R)-N-Amidino-2-[2-(4-chlorostyryl)-6-methylquinazolin-4-yl]aminocyclohexylamine Dihydrochloride
Cation FAB-MS m/z: 435[M+H]$^+$
Element analytical value (as $C_{24}H_{27}N_6Cl \cdot 2HCl \cdot 2H_2O$)
Calculated value (%) C: 53.00; H: 6.12; N: 15.45. Found value (%) C: 52.95; H: 5.95; N: 15.40.
Optical rotation $[\alpha]_D^{20}=-86.7°$ (c=1.1, methanol)

EXAMPLE 15
N-Amidino-N'-[6-tert-butyl-2-(4-chlorostyryl)quinazolin-4-yl]-1,6-hexanediamine Dihydrochloride
Appearance: pale red powder

EXAMPLE 16
N-Amidino-N'-[2-(4-chlorostyryl)-6-methoxyquinazolin-4-yl]-1,6-hexanediamine Dihydrochloride
Cation FAB-MS m/z: 453[M+H]$^+$
Appearance: pale yellow powder
Element analytical value (as $C_{24}H_{29}ClN_6O.2HCl.H_2O$) Calculated value (%) C: 53.00; H: 6.12; N: 15.45. Found value (%) C: 52.73; H: 5.99; N: 15.64.

EXAMPLE 17
N-Amidino-N'-[2-(4-chlorostyryl)-6,7-dimethylquinazolin-4-yl]-1,5-pentanediamine Dihydrochloride
Cation FAB-MS m/z: 437[M+H]$^+$
Element analytical value (as $C_{24}H_{29}ClN_6.3HCl$) Calculated value (%) C: 52.76; H: 5.90; N: 15.38. Found value (%) C: 52.45; H: 6.12; N: 15.10.

EXAMPLE 18
N-Amidino-N'-[2-(4-chlorostyryl)-6-isopropylquinazolin-4-yl]-1,6-hexanediamine Dihydrochloride
Cation FAB-MS m/z: 465[M]$^+$
Element analytical value (as $C_{26}H_{33}ClN_6.2HCl.1.4H_2O$) Calculated value (%) C: 55.45; H: 6.77; N: 14.92. Found value (%) C: 55.50; H: 6.61; N: 14.82.

EXAMPLE 19
cis-N-Amidino-N'-[2-(4-chlorostyryl)-6-methylquinazolin-4-yl]-1,4-cyclohexanediamine Dihydrochloride
Cation FAB-MS m/z: 435[M+H]$^+$
Element analytical value (as $C_{24}H_{27}ClN_6.2HCl.H_2O$) Calculated value (%) C: 53.00; H: 6.11; N: 15.45. Found value (%) C: 53.50; H: 6.08; N: 14.92.

EXAMPLE 20
cis-N-Amidino-2-[2-(4-chlorostyryl)-6,7-dimethyl-quinazolin-4-yl]aminocyclohexylamine Dihydrochloride
Cation FAB-MS m/z: 449[M+H]$^+$

EXAMPLE 21
cis-N-Amidino-3-[2-(4-chlorostyryl)-6-methylquinazolin-4-yl]aminocyclohexylamine Dihydrochloride
Cation FAB-MS m/z: 435[M+H]$^+$
Element analytical value (as $C_{24}H_{27}ClN_6.2HCl.2H_2O$) Calculated value (%) C: 53.00; H: 6.12; N: 15.45. Found value (%) C: 52.52; H: 5.79; N: 15.23.

EXAMPLE 22
trans-N-Amidino-3-[2-(4-chlorostyryl)-6-methyl-quinazolin-4-yl]aminocyclohexylamine Dihydrochloride
Cation FAB-MS m/z: 435[M+H]$^+$

EXAMPLE 23
N-Amidino-N'-{6-methoxy-2-[2-(2-pyridyl)ethenyl]quinazolin-4-yl}-1,6-hexanediamine Dihydrochloride
Appearance: yellow crystals
Cation FAB-MS m/z: 420[M+H]$^+$
Element analytical value (as $C_{23}H_{29}N_7O.3HCl.3H_2O$) Calculated value (%) C: 47.39; H: 6.57; N: 16.82. Found value (%) C: 47.32; H: 6.29; N: 16.89.

EXAMPLE 24
(1R,2S)-N-Amidino-2-[2-(4-chlorostyryl)-6-methoxy-quinazolin-4-yl]aminocyclohexylamine Dihydrochloride
Appearance: pale yellow powder
Cation FAB-MS m/z: 451[M+H]$^+$
Element analytical value (as $C_{24}H_{27}ClN_6O.2HCl.0.5H_2O$) Calculated value (%) C: 54.09; H: 5.67; N: 15.77. Found value (%) C: 53.71; H: 5.60; N: 15.65.
Optical rotation $[\alpha]_D^{20}$=+81.7° (c=1.1, methanol)

EXAMPLE 25
(1S,2R)-N-Amidino-2-[2-(4-chlorostyryl)-6-methoxyquinazolin-4-yl]aminocyclohexylamine Dihydrochloride
Appearance: pale yellow powder
Cation FAB-MS m/z: 451[M+H]$^+$
Element analytical value (as $C_{24}H_{27}ClN_6O.2HCl.H_2O$) Calculated value (%) C: 53.19; H: 5.77; N: 15.51. Found value (%) C: 53.37; H: 5.54; N: 15.61.
Optical rotation $[\alpha]_D^{20}$-77.6° (c=0.6, methanol)

EXAMPLE 26
N-Amidino-N'-[2-(4-chlorostyryl)quinazolin-4-yl]-1,4-bis(aminomethyl)cyclohexane Dihydrochloride
Appearance: pale red powder
Cation FAB-MS m/z: 449[M+H]$^+$
Element analytical value (as $C_{25}H_{29}ClN_6.2HCl.H_2O$) Calculated value (%) C: 55.62; H: 6.16; N: 15.56. Found value (%) C: 55.64; H: 6.16; N: 15.02.

EXAMPLE 27
N-Amidino-N'-[2-(4-chlorostyryl)benzo[g]quinazolin-4-yl]-1,6-hexanediamine Dihydrochloride
Cation FAB-MS m/z: 473[M+H]$^+$
Appearance: orange powder
Element analytical value (as $C_{27}H_{29}ClN_6.3HCl.0.5H_2O$) Calculated value (%) C: 54.84; H: 5.62; N: 14.21. Found value (%) C: 55.11; H: 5.65; N: 14.37.

EXAMPLE 28
cis-N-Amidino-2-[2-(4-chlorostyryl)-6-isopropyl-quinazolin-4-yl]aminocyclohexylamine Dihydrochloride
Cation FAB-MS m/z: 464[M+H]$^+$
Element analytical value (as $C_{26}H_{31}ClN_6.2.0HCl.2H_2O$) Calculated value (%) C: 54.60; H: 6.52; N: 14.69. Found value (%) C: 54.82; H: 6.20; N: 14.85.

EXAMPLE 29
N-Amidino-N'-[2-(4-chlorostyryl)-6-methylquinazolin-4-yl]-1,4-bis(aminomethyl)cyclohexane Dihydrochloride
Cation FAB-MS m/z: 463[M+H]$^+$
Element analytical value (as $C_{26}H_{31}ClN_6.2HCl.1.5H_2O$) Calculated value (%) C: 55.47; H: 6.45; N: 14.93. Found value (%) C: 55.81; H: 6.52; N: 14.72.

EXAMPLE 30
cis-N-Amidino-2-[2-(4-chlorostyryl)-6-hydroxyquinazolin-4-yl]aminocyclohexylamine Dihydrochloride
Appearance: pale green powder
Cation FAB-MS m/z: 437[M+H]$^+$
Element analytical value (as $C_{23}H_{25}ClN_6O.3HCl.1.5H_2O$) Calculated value (%) C: 48.40; H: 5.30; N: 14.37. Found value (%) C: 48.18; H: 5.45; N: 14.66.

EXAMPLE 31
cis-N-Amidino-2-{6-methyl-2-[2-(4-pyridyl)ethenyl]quinazolin-4-yl}aminocyclohexylamine Trihydrochloride Cation FAB-MS m/z: 402[M+H]$^+$ Element analytical value (as $C_{23}H_{27}N_7.3HCl.6H_2O$) Calculated value (%) C: 44.63; H: 6.84; N: 15.84. Found value (%) C: 45.00; H: 6.59; N: 15.65.

EXAMPLE 32
cis-N-Amidino-2-[2-(4-chlorobenzoylamino)-6-methylquinazolin-4-yl]aminocyclohexylamine Dihydrochloride Cation FAB-MS m/z: 452[M+H]$^+$

EXAMPLE 33
cis-N-Amidino-2-[2-(4-chlorostyryl)-6-ethoxyquinazolin-4-yl]aminocyclohexylamine Dihydrochloride Appearance: pale yellow powder Cation FAB-MS m/z: 465[M+H]$^+$ Element analytical value (as $C_{25}H_{29}ClN_6O.3HCl.H_2O$) Calculated value (%) C: 51.19; H: 5.86; N: 13.90. Found value (%) C: 50.69; H: 5.79; N: 14.19.

EXAMPLE 34
cis-N-Amidino-2-{6-methoxy-2-[2-(3-pyridyl)ethenyl]quinazolin-4-yl}aminocyclohexylamine Trihydrochloride Cation FAB-MS m/z: 418[M+H]$^+$ Element analytical value (as $C_{23}H_{27}N_7O.3HCl.H_2O$) Calculated value (%) C: 50.70; H: 5.92; N: 18.00. Found value (%) C: 50.57; H: 5.85; N: 17.98.

EXAMPLE 35
(1R,2S)-cis-N-Amidino-2-{6-methoxy-2-[2-(3-pyridyl)ethenyl]quinazolin-4-yl}aminocyclohexylamine Trihydrochloride Cation FAB-MS m/z: 418[M+H]$^+$

EXAMPLE 36
(1S,2R)-cis-N-Amidino-2-{6-methoxy-2-[2-(3-pyridyl)ethenyl]quinazolin-4-yl}aminocyclohexylamine Trihydrochloride Cation FAB-MS m/z: 418[M+H]$^+$

EXAMPLE 37
(1R,2S)-N-Amidino-2-[2-(4-chlorostyryl)-6-methoxyquinazolin-4-yl]aminocyclopentylamine Dihydrochloride Cation FAB-MS m/z: 437[M+H]$^+$ Element analytical value (as $C_{23}H_{25}ClN_6O.2HCl.H_2O$) Calculated value (%) C: 52.33; H: 5.54; N: 15.92. Found value (%) C: 52.72; H: 5.24; N: 16.07.

Optical rotation $[\alpha]_D^{20}$=−52.3° (c=1.0, methanol)

EXAMPLE 38
(1S,2R)-N-Amidino-2-[2-(4-chlorostyryl)-6-methoxyquinazolin-4-yl]aminocyclopentylamine Dihydrochloride Cation FAB-MS m/z: 437[M+H]$^+$ Element analytical value (as $C_{23}H_{25}ClN_6O.2HCl.H_2O$) Calculated value (%) C: 52.33; H: 5.54; N: 15.92. Found value (%) C: 52.42; H: 5.34; N: 15.98.

EXAMPLE 39
cis-N-amidino-2-{6-methoxy-2-[2-(2-pyridyl)ethenyl]quinazolin-4-yl}aminocyclohexylamine Trihydrochloride Cation FAB-MS m/z: 418[M+H]$^+$ Element analytical value (as $C_{23}H_{27}N_7O.3HCl.H_2O$) Calculated value (%) C: 50.70; H: 5.92; N: 18.00. Found value (%) C: 50.58; H: 5.75; N: 18.10.

EXAMPLE 40
(1R,2S)-cis-N-Amidino-2-{6-methoxy-2-[2-(2-pyridyl)ethenyl]quinazolin-4-yl}aminocyclohexylamine Trihydrochloride Cation FAB-MS m/z: 418[M+H]$^+$

EXAMPLE 41
(1S,2R)-cis-N-Amidino-2-{6-methoxy-2-[2-(2-pyridyl)ethenyl]quinazolin-4-yl}aminocyclohexylamine Trihydrochloride Cation FAB-MS m/z: 418[M+H]$^+$

EXAMPLE 42
cis-N-Amidino-2-{6-Methoxy-2-[2-(4-pyridyl)ethenyl]quinazolin-4-yl}aminocyclohexylamine Trihydrochloride Cation FAB-MS m/z: 418[M+H]$^+$

EXAMPLE 43
cis-N-Amidino-2-[6-methoxy-2-(2-methoxystyryl)quinazolin-4-yl]aminocyclohexylamine Dihydrochloride Cation FAB-MS m/z: 447[M+H]$^+$ Element analytical value (as $C_{25}H_{30}N_6O_2.3HCl$) Calculated value (%) C: 54.01; H: 5.98; N: 15.12. Found value (%) C:. 54.11; H: 6.22; N: 15.14.

EXAMPLE 44
cis-N-Amidino-N'-{6-methoxy-2-[2-(2-pyridyl)ethenyl]quinazolin-4-yl}-1,4-bis(aminomethyl)cyclohexane Trihydrochloride Appearance: orange powder Cation FAB-MS m/z: 446[M+H]$^+$

EXAMPLE 45
trans-N-Amidino-N'-{6-methoxy-2-[2-(2-pyridyl)ethenyl]quinazolin-4-yl}-1,4-bis(aminomethyl)cyclohexane Trihydrochloride Appearance: orange powder Cation FAB-MS m/z: 446[M+H]$^+$

EXAMPLE 46
N-Amidino-N'-{6-methyl-2-[2-(2-pyridyl)ethenyl]quinazolin-4-yl}-1,6-hexanediamine Trihydrochloride Cation FAB-MS m/z: 404[M+H]$^+$ Element analytical value (as $C_{23}H_{29}N_7.3HCl.2H_2O$) Calculated value (%) C: 50.33; H: 6.61; N: 17.86. Found value (%) C: 50.93; H: 6.69; N: 17.26.

EXAMPLE 47
N-Amidino-N'-{6-methyl-2-[2-(2-pyridyl)ethenyl]quinazolin-4-yl}-1,8-octanediamine Trihydrochloride Appearance: yellow powder Cation FAB-MS m/z: 432[M+H]$^+$ Element analytical value (as $C_{25}H_{33}N_7.3HCl.H_2O$) Calculated value (%) C: 53.72; H: 6.85; N: 17.54. Found value (%) C: 53.83; H: 7.03; N: 17.03.

EXAMPLE 48
N-Amidino-6-{6-methoxy-2-[2-(2-pyridyl)ethenyl]quinazolin-4-yl}aminoheptylamine Trihydrochloride Appearance: yellow powder Cation FAB-MS m/z: 434[M+H]$^+$ Element analytical value (as $C_{24}H_{31}N_7O.3HCl.1.5H_2O$) Calculated value (%) C: 65.28; H: 6.14; N: 12.18. Found value (%) C: 65.23; H: 5.92; N: 12.12.

EXAMPLE 49

N-[2-(4-chlorostyryl)quinazolin-4-yl]-N'-(2-pyrimidyl)piperazine Dihydrochloride The title compound was obtained as pale yellow powder by the method similar to that in Example 3.

Cation FAB-MS m/z: 429[M+H]$^+$

Element analytical value (as $C_{24}H_{21}ClN_6$·3HCl) Calculated value (%) C: 56.33; H: 6.47; N: 11.43. Found value (%) C: 56.05; H: 6.31; N: 11.36.

EXAMPLE 50 cis-N-[2-(4-Chlorostyryl)-6-methoxyquinazolin-4-yl]-2-guanidinomethylcyclohexylamine Dihydrochloride The title compound was obtained by the method similar to that in Example 4.

Cation FAB-MS m/z: 465[M+H]$^+$

Element analytical value (as $C_{25}H_{29}ClN_6O$·3HCl) Calculated value (%) C: 52.28; H: 5.62; N: 14.63. Found value (%) C: 52.24; H: 5.66; N: 14.27.

EXAMPLE 51

N-2-(2-Imidazolinyl)-N'-[2-(4-chlorostyryl)-6-methylquinazolin-4-yl]-1,6-hexanediamine Dihydrochloride The title compound was obtained as white powder by the method similar to that in Example 5.

Melting point: 305° C.

EXAMPLE 52

N-[2-(4-Chlorostyryl)quinazolin-4-yl]-1,2-ethanediamine Dihydrochloride

Appearance: pale red powder

Cation FAB-MS m/z: 367[M+H]$^+$

Element analytical value (as $C_{19}H_{19}ClN_6$·2HCl·H$_2$O) Calculated value (%) C: 49.85; H: 5.06; N: 18.36. Found value (%) C: 49.97; H: 4.97; N: 18.26.

EXAMPLE 53

N-Amidino-N'-[2-(4-chlorostyryl)quinazolin-4-yl]-1,6-hexanediamine Dihydrochloride Appearance: white powder Cation FAB-MS m/z: 423[M+H]$^+$

EXAMPLE 54

N-Amidino-N'-[2-(4-chlorostyryl)-6-methylquinolin-4-yl]-1,6-hexanediamine Dihydrochloride Appearance: pale yellow powder Cation FAB-MS m/z: 436[M+H]$^+$ Element analytical value (as $C_{25}H_{30}ClN_5$·2HCl·0.7H$_2$O) Calculated value (%) C: 57.58; H: 6.45; N: 13.43. Found value (%) C: 57.48; H: 6.32; N: 13.34.

EXAMPLE 55

N-Amidino-N'-[2-(4-chlorostyryl)quinolin-4-yl]-1,6-hexanediamine Dihydrochloride Appearance: pale yellow powder Cation FAB-MS m/z: 422[M+H]$^+$

EXAMPLE 56 cis-N-Amidino-2-[2-(4-chlorostyryl)-6-methylquinolin-4-yl]aminocyclohexylamine Dihydrochloride Appearance: white powder Cation FAB-MS m/z: 434[M+H]$^+$ Element analytical value (as $C_{21}H_{28}ClN_5$·2HCl·1.5H$_2$O) Calculated value (%) C: 56.24; H: 6.23; N: 13.12. Found value (%) C: 56.14; H: 6.02; N: 13.08.

EXAMPLE 57 cis-N-Amidino-2-[2-(4-chlorostyryl)-6-methoxyquinolin-4-yl]aminocyclohexylamine Dihydrochloride Appearance: pale yellow powder Cation FAB-MS m/z: 450[M+H]$^+$ Element analytical value (as $C_{25}H_{28}ClN_5O$·3HCl·H$_2$O) Calculated value (%) C: 52.01; H: 5.76; N: 12.13. Found value (%) C: 52.00; H: 5.59; N: 12.01.

EXAMPLE 58 cis-N-Amidino-2-[3-(4-chlorostyryl)isoquinolin-1-yl]aminocyclohexylamine Dihydrochloride Appearance: pale yellow powder Cation FAB-MS m/z: 420[M+H]$^+$

EXAMPLE 59

N-Amidino-4-{6-methyl-2-[2-(2-pyridyl)ethenyl]quinazolin-4-yl]aminomethyl-benzylamine Trihydrochloride Appearance: white powder Cation FAB-MS m/z: 424[M+H]$^+$ Element analytical value (as $C_{25}H_{25}N_7$·3HCl·2H$_2$O) Calculated value (%) C: 52.78; H: 5.66; N: 17.23. Found value (%) C: 53.28; H: 5.36; N: 17.09.

EXAMPLE 60

N-(N-Isobutyl-N'-phenyl)amidino-N'-{6-methoxy-2-[2-(2-pyridyl)ethenyl]quinazolin-4-yl}-1,6-hexanediamine Trihydrochloride Step 1

N-[6-{6-Methoxy-2-[2-(2-pyridyl)ethenyl]quinazolin-4-yl}amino]hexyl-N'-phenyl-thiourea A solution of 135 mg of N-{6-methoxy-2-[2-(2-pyridyl)ethenyl]quinazolin-4-yl}-1,6-hexanediamine in methylene chloride was combined with 58 mg of phenylisocyanate, and stirred at room temperature for 2 hours. After the reaction solution was distilled off, the residue was purified by column chromatography on silica gel (chloroform:methanol=50:1) to obtain 174 mg of the desirable compound.

Step 2

N-[6-{6-Methoxy-2-[2-(2-pyridyl)ethenyl]quinazolin-4-yl}amino]hexyl-N'-phenyl-S-methylisothiourea A solution of 10 mg in 3 mL of methylene chloride was combined with an excessive amount of methyl iodide, and stirred for 15 hours. After the reaction solution was distilled off, the residue was purified by column chromatography on silica gel (chloroform:methanol:aqueous ammonia=10:1:0.1) to obtain 11 mg of the desirable compound.

Step 3

N-(N-Isobutyl-N'-phenyl)amidino-N'-{6-methoxy-2-[2-(2-pyridyl)ethenyl]quinazolin-4-yl}-1,6-hexanediamine Trihydrochloride A solution of 11 mg in 3 mL of ethanol was combined with an excessive amount of isobutylamine, and heated under reflux for 15 hours. After the reaction solution was distilled off, the residue was purified by column chromatography on silica gel (chloroform:mathanol:aqueous ammonia=10:1:0.1), and then treated with a 4N solution of hydrogen chloride in ethyl acetate to obtain 13 mg of the desirable compound.

Cation FAB-MS m/z: 552[M+H]$^+$

The compounds of the following Example 62 and Example 63 were produced by the method similar to that in Example 60.

EXAMPLE 61
2-Guanidinoethoxy-N-{6-methyl-2-[2-(2-pyridyl)ethenyl]quinazolin-4-yl}ethylamine Trihydrochloride
Appearance: pale yellow powder
Cation FAB-MS m/z: 392[M+H]+

EXAMPLE 62
N-(N-Methyl-N'-phenyl)amidino-N'-{6-methoxy-2-[2-(2-pyridyl)ethenyl]quinazolin-4-yl}-1,6-hexanediamine Trihydrochloride
Appearance: pale yellow powder
Cation FAB-MS m/z: 510[M+H]+

EXAMPLE 63
N-(N-Ethyl-N'-methyl)amidino-N'-{6-methoxy-2-[2-(2-pyridyl)ethenyl]quinazolin-4-yl}-1,6-hexanediamine Trihydrochloride
Cation FAB-MS m/z: 462[M+H]+

EXAMPLE 64
2-Guanidinopropyloxy-N-{6-methyl-2-[2-(2-pyridyl)ethenyl]quinazolin-4-yl}ethylamine Trihydrochloride
Appearance: yellow powder
Cation FAB-MS m/z: 406[M+H]+

EXAMPLE 65
3-Guanidinoethoxy-N-{6-methyl-2-[2-(2-pyridyl)ethenyl]quinazolin-4-yl}propylamine Trihydrochloride
Appearance: pale yellow powder
Cation FAB-MS m/z: 406[M+H]+

EXAMPLE 66
N-Amidino-2-{6-methoxy-2-[2-(2-pyridyl)ethenyl]quinazolin-4-yl}aminoethyl-phenylethylamine Trihydrochloride
Appearance: yellow powder
Cation FAB-MS m/z: 468[M+H]+
Element analytical value (as $C_{27}H_{29}N_7O.3HCl$) Calculated value (%) C: 56.21; H: 5.59; N: 16.99. Found value (%) C: 55.92; H: 5.59; N: 16.28.

EXAMPLE 67
trans-4-Guanidinomethyl-cis-2-methyl-N-{6-methoxy-2-[2-(2-pyridyl)ethenyl]quinazolin-4-yl}cyclohexylamine Trihydrochloride
Appearance: yellow powder
Cation FAB-MS m/z: 446[M+H]+
Element analytical value (as $C_{25}H_{31}N_7O.3HCl.H_2O$) Calculated value (%) C: 49.31; H: 6.62; N: 16.10. Found value (%) C: 49.60; H: 6.42; N: 16.01.

EXAMPLE 68
cis-4-Guanidinomethyl-cis-2-methyl-N-{6-methoxy-2-[2-(2-pyridyl)ethenyl]quinazolin-4-yl}cyclohexylamine Trihydrochloride
Appearance: yellow powder
Cation FAB-MS m/z: 446[M+H]+
Element analytical value (as $C_{25}H_{31}N_7O.3HCl.2.5H_2O$) Calculated value (%) C: 50.05; H: 6.55; N: 16.34. Found value (%) C: 49.87; H: 6.30; N: 16.22.

EXAMPLE 69
(1R,2S)-N-Amidino-2-(2-(4-chlorobenzoylamino)-6-methoxyquinazolin-4-yl)aminocyclohexylamine Dihydrochloride Step 1
(1R,2S)-N-tert-Butoxycarbonyl-2-(2-chloro-6-methoxyquinazolin-4-yl)aminocyclohexylamine A solution of 710 mg of 2,4-dichloro-6-methoxyquinazoline in 20 mL of methylene chloride was combined with 471 mg of triethylamine and 750 mg of (1S,2R)-2-tert-butoxycarbonylaminocyclohexylamine, and stirred at room temperature for 48 hours. After concentrating, the mixture was combined with water, extracted with methylene chloride, and dried. After solvent was distilled off, the residue was purified by column chromatography on silica gel (chloroform:methanol 20:1) to obtain 1.20 g of the desirable compound.

Step 2
(1R,2S)-N-tert-Butoxycarbonyl-2-[2-(4-methoxybenzylamino)-6-methoxyquinazolin-4-yl]aminocyclohexylamine Under argon atmosphere, a solution of 1.75 g of (1R,2S)-N-tert-butoxycarbonyl-2-(2-chloro-6-methoxyquinazolin-4-yl)aminocyclohexylamine and 1.47 g of 4-methoxybenzylamine in 100 mL of anhydrous toluene was combined with 97 mg of palladium acetate, 268 mg of 2,2'-bis(diphenylphosphino)-1,1'-binaphthyl and 1.03 g of sodium tert-butoxide, and stirred at 70° C. for 5 hours. The reaction solvent was concentrated, and then combined with water, extracted with chloroform, and dried. After the solvent was distilled off, the residue was purified by column chromatography on silica gel (chloroform:methanol=20:1) to obtain 1.62 g of the desirable compound.

Step 3
(1R,2S)-N-[N,N'-Bis(tert-butoxycarbonyl)]amidino-2-[2-(4-methoxybenzylamino)-6-methoxyquinazolin-4-yl]aminocyclohexylamine A solution of 1.70 g of (1R,2S)-N-tert-butoxycarbonyl-2-[2-(4-methoxybenzylamino)-6-methoxyquinazolin-4-yl]aminocyclohexylamine in 30 mL of methylene chloride was combined with 10 mL of trifluoroacetic acid with cooling in ice, and stirred for 2 hours. The reaction solution was neutralized with a saturated solution of sodium hydrogen carbonate, extracted with methylene chloride, and dried. After the solvent was distilled off, a solution of the residue in 30 mL of methylene chloride was combined with 1.18 g of N,N'-bis(tert-butoxycarbonyl)-1H-pyrazole-1-carboxyamidine, and stirred at room temperature for 15 hours. The reaction solution was combined with water, extracted with methylene chloride, and dried. After the solvent was distilled off, the residue was purified by column chromatography on silica gel (chloroform:methanol=20:1) to obtain 1.86 g of the desirable compound.

Step 4
(1R,2S)-N-[N,N'-Bis(tert-butoxycarbonyl)]amidino-2-(2-amino-6-methoxyquinazolin-4-yl)aminocyclohexylamine A solution of 1.76 g of (1R,2S)-N-[N,N'-bis(tert-butoxycarbonyl)]amidino-2-[2-(4-methoxybenzylamino)-6-methoxyquinazolin-4-yl]aminocyclohexylamine in 80 mL of methylene chloride was combined with 3.17 g of N-methylmorpholine-N-oxide and 95 mg of tetrapropylammonium perruthenate, and stirred for 9 hours. The reaction solution was combined with water, extracted with methylene chloride, and dried. After the solvent was distilled off, the residue was purified by column chromatography on silica gel (chloroform:methanol 10:1) to obtain 0.95 g of the desirable compound.

Step 5
(1R,2S)-N-[N,N'-Bis(tert-butoxycarbonyl)]amidino-2-[2-(4-chlorobenzoylamino)-6-methoxyquinazolin-4-yl]aminocyclohexylamine A solution of 366 mg of N,N-diisopropylethylamine in 10 mL of methylene chloride was combined with 60 mg of 4-dimethylaminopyridine and 0.156 mL of 4-chlorobenzoyl chloride. This was treated dropwise with a solution of 500 mg of (1R,2S)-N-[N,N'-bis(tert-butoxycarbonyl)]amidino-2-(2-amino-6-methoxyquinazolin-4-yl)aminocyclohexylamine in 10 mL of methylene chloride, and stirred at room temperature for 3 hours. The reaction solution was combined with water, extracted with methylene chloride, and dried. After the solvent was distilled off, the residue was purified by column chromatography on silica gel (chloroform:methanol=30:1) to obtain 560 mg of the desirable compound.

Step 6

(1R,2S)-N-Amidino-2-{[2-(4-chlorobenzoylamino)-6-methoxyquinazolin-4-yl]amino}cyclohexylamine Dihydrochloride A solution of 450 mg of (1R,2S)-N-[N,N'-bis(tert-butoxycarbonyl)]amidino-2-[2-(4-chlorobenzoylamino)-6-methoxyquinazolin-4-yl]aminocyclohexylamine in 5 mL of methanol and 5 mL of chloroform was combined with 5 mL of a 4N solution of hydrogen chloride in ethyl acetate, and reacted at 50° C. for 72 hours. After concentrating, treatment was performed with methanol-ethyl ether to obtain 260 mg of the desirable compound as colorless powder.

Cation FAB-MS m/z: 468[M+H]$^+$

Element analytical value (as $C_{23}H_{26}ClN_7O_2 \cdot 2HCl \cdot 1.5H_2O$) Calculated value (%) C: 48.64; H: 5.50; N: 17.26. Found value (%) C: 48.87; H: 5.38; N: 17.29.

Optical rotation $[\alpha]_D^{20}$=+64.97 (c=1.0, methanol)

The compound of the following Example 70 was produced by the method similar to that in Example 69.

EXAMPLE 70

(1S,2R)-N-Amidino-2-{[2-(4-chlorobenzoylamino)-6-methoxyquinazolin-4-yl]amino}cyclohexylamine Dihydrochloride Cation FAB-MS m/z: 468[M+H]$^+$ Element analytical value (as $C_{23}H_{26}ClN_7O_2 \cdot 2HCl \cdot 3H_2O$) Calculated value (%) C: 46.43; H: 5.76; N: 16.48. Found value (%) C: 46.41; H: 5.56; N: 16.50.

Optical rotation $[\alpha]_D^{20}$=−65.98° (c=1.0, methanol)

TEST EXAMPLE 1

Nociceptin Receptor Binding Assay

A cell membrane suspension obtained from a human nociceptin-expressing cell was prepared so that it contained 5 to 10 μg/mL of the membrane protein in a Tris buffer [50 mM Tris-HCl (pH 7.8), 5 mM MgCl$_2$, 1 mM EGTA, 0.1% BSA]. To this, [$^3$H]nociceptin (diluted at the final concentration of 0.08 nM with the Tris buffer) and a tested substance were added and the mixture was incubated at 25° C. for 60 minutes. Using a cell harvester and a washing solution [50 mM Tris-HCl (pH 7.8), 4° C.], the membrane was recovered onto a GF/B filter which had been pretreated with 0.3% PEI, which was then washed further 4 times. The filter was transferred to a vial, to which a scintillator was added, and the radioactivity was measured using a liquid scintillation counter. Noted that a non-specific binding was regarded as a binding in the presence of 10 μM nociceptin, and a specific binding was obtained by subtracting the non-specific binding from the total binding. From a ratio of binding inhibition in the presence of the tested substance, an IC$_{50}$ value was obtained, and was then used together with the K$_d$ value for [$^3$H]nociceptin to calculate the K$_i$ value for the tested substance. The results were shown in Table 1.

TABLE 1

| Substances tested (Example No.) | Affinity for nociceptin receptors K$_i$ (μM) |
|---|---|
| 2 | 0.006 |
| 4 | 0.008 |
| 16 | 0.009 |
| 23 | 0.003 |
| 44 | 0.007 |
| 46 | 0.003 |
| 66 | 0.004 |
| 68 | 0.003 |

TEST EXAMPLE 2

μ-Receptor Binding Assay

A human μ-receptor-expressing cell membrane preparation (Receptor Biology) was prepared so that it contained 8.5 μg/mL of the membrane protein in a Tris buffer [50 mM Tris-HCl (pH 7.8), 5 MM MgCl$_2$, 1 mM EGTA, 0.1% BSA]. To this, [$^3$H]diprenorphine (diluted at the final concentration of 0.13 nM with the Tris buffer) and a tested substance were added and the mixture was incubated at 25° C. for 90 minutes. Using a cell harvester and a washing solution [50 mM Tris-HCl (pH 7.8), 4° C.], the membrane was recovered onto a GF/B filter which had been pretreated with 0.3% PEI, which was then washed further 4 times. The filter was transferred to a vial, to which a scintillator was added, and the radioactivity was measured using a liquid scintillation counter. A non-specific binding was regarded as a binding in the presence of 100 μM naloxone, and a specific binding was obtained by subtracting the non-specific binding from the total binding. From a ratio of binding inhibition in the presence of the tested substance, and IC$_{50}$ value was obtained, and was then used together with the K$_d$ value for [$^3$H]diprenorphine to calculate the K$_i$ value of the tested substance. The results were shown in Table 2.

表 2

| Substances tested (Example No.) | Affinity for μ-receptor K$_i$ (μM) |
|---|---|
| 2 | 0.193 |
| 4 | 0.063 |
| 16 | 0.038 |
| 23 | 0.019 |
| 44 | 0.030 |
| 46 | 0.023 |
| 66 | 0.022 |
| 68 | 0.032 |

As apparent from Table 1 and Table 2, each compound of the present invention had a selective binding effect on the nociceptin receptor.

TEST EXAMPLE 3

Acetic Acid-Writhing Test in Mice

Ten male mice (Slc:ddY, 4 to 5 weeks old) were assigned to each group. The dorsal skin of each mouse was incised laterally in a length of approximately 3 cm, and after acclimatizing for 30 minutes or longer a 27G needle fitted on the tip of a silicone tube connected to a microsyringe was inserted into a position around L3–L4, through which 5 μL of a drug solution was infused, whereby effecting an administration into a spinal subarachnoid cavity. The tested substance was dissolved in physiological saline, and administered at 10 nmol/animal. In a control group, physiological saline was administered similarly.

A mouse which had been fasting since the day before the experiment was placed in an observation cage (20×20×15 cm), where it was allowed to be acclimatized over a period of 30 minutes or longer, and then received 100 μL per 10 g body weight of a 0.6% acetic acid solution intraperitoneally via a 27G needle. The number of the writhing reactions with stretching the abdomen was counted over 20 minutes after the administration of acetic acid, and the obtained data were represented as means±standard errors. Only the screening data were subjected to the test for a significant difference by a t test between the two groups of the control and a treatment group or by one-way analysis of variance among multiple groups followed by Dunnett's multiple comparison test, and the significant difference was regarded to be present when $p<0.05$. The results were shown in Table 3.

| Acetic Acid-Writhing Test in Mice (Number of writhings) | | | | | |
|---|---|---|---|---|---|
| Intrathecal administration Animal No. | saline | Ex. 4 10 nmol, | Ex. 23 10 nmol, | Ex. 46 10 nmol, | Ex. 48 10 nmol |
| 1 | 0 | 12 | 18 | 0 | 6 |
| 2 | 19 | 11 | 28 | 4 | 16 |
| 3 | 30 | 0 | 0 | 0 | 1 |
| 4 | 18 | 1 | 3 | 0 | 14 |
| 5 | 18 | 13 | 0 | 9 | 12 |
| 6 | 23 | 18 | 14 | 0 | 7 |
| 7 | 4 | 12 | 0 | 13 | 0 |
| 8 | 27 | 10 | 0 | 6 | 0 |
| 9 | 16 | 0 | 0 | 3 | 0 |
| 10 | 0 | 2 | 6 | 10 | 0 |
| 11 | 32 | | | | |
| 12 | 0 | | | | |
| 13 | 25 | | | | |
| 14 | 20 | | | | |
| 15 | 33 | | | | |
| Mean | 17.67 | 7.90 | 6.90 | 4.50 | 5.60 |
| Standard error | 3.00 | 2.06 | 3.11 | 1.52 | 2.02 |

As apparent from Table 3, each compound of the present invention was revealed to reduce the number of significant writhing reactions thereby exerting an analgesic effect.

FORMULATION EXAMPLE 1

100 g of the compound of Example 70, 292 g of D-mannitol, 120 g of corn starch and 28 g of a low substituted hydroxypropyl cellulose are placed in a fluidized bed granulator (STREA; PAUREC) and granulated with spraying a certain amount of a 5% aqueous solution of hydroxypropyl cellulose. After drying and then milling by a grinding/milling machine (COMIL; PAULEC), a certain amount of magnesium stearate is admixed by a mixer (BOHRE container mixer Model MC20, KOTOBUKI-GIKEN), and the mixture is subjected to a rotary tablet compacting machine (CORRECT 12HUK; KIKUSUI) to mold into tablets each 7 mm in diameter weighing 140 mg per tablet, thereby obtaining a tablet containing 25 mg of the compound of the present invention.

FORMULATION EXAMPLE 2

75 g of the compound of Example 70, 180 g of lactose, 75 g of corn starch and 18 g of croscarmellose calcium are placed in a stirring granulator (vertical granulator model VG-01), combined with a certain amount of a 5% aqueous solution of hydroxypropylmethyl cellulose and granulated, and then dried by a fluidized bed granulating drier (STREA; PAUREC) and then milled by a grinding/milling machine (COMIL; manufactured by PAULEC). Each 120 mg of the milled material is filled into a #3 capsule using a capsule filling machine (capsule filler; SHIONOGI QUALICAPS), thereby obtaining a capsule containing 25 mg of the compound of the present invention.

FORMULATION EXAMPLE 3

2.5 g of the compound of Example 70 and 4.5 g of sodium chloride are weighed, combined with 450 mL of water for injection and sttired and dissolved, and adjusted at pH 6.5 with 0.1 mol/L hydrochloric acid or 0.1 mol/L sodium hydroxide. Then water for injection is added to make the entire quantity 500 mL. The solution thus formulated is filtered under pressure through a membrane filter (pore size: 0.22 μm). Then 5.3 mL is filled aseptically to a sterilized 5 mL brown ampoule, thereby obtaining an injection formulation containing 25 mg of the compound of the present invention. The procedure from the preparation through the filling are performed aseptically.

FORMULATION EXAMPLE 4

99.75 g of UITEPSOL H-15 (manufactured by HIRTH) is dissolved at 45° C. and combined with 0.25 g of the compound of Example 70, and dispersed by stirring. This was infused into a 1 g suppository mold carefully to prevent sedimentation while hot, solidified and taken out from the mold, thereby obtaining a suppository containing 25 mg of the compound of the present invention.

INDUSTRIAL APPLICABILITY

Since a compound of the present invention has an excellent nociceptin receptor binding ability, it can be used for a prolonged period safely as a therapeutic agent against a dolorous disease such as a pain, migraine, rheumatoid arthritis and neuralgia and as an agent for overcoming the resistance to morphine or the like.

What is claimed is:

1. A compound represented by the following general formula (1):

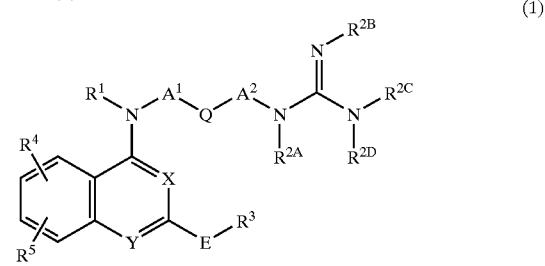

(1)

wherein X and Y represent a nitrogen atom;

$R^1$ represents a hydrogen atom or alkyl;

$A^1$ and $A^2$ are same or different and each represents (1) a single bond or (2) a divalent aliphatic hydrocarbon group which may be substituted and which may have 1 to 3 unsaturated bonds at any positions (such aliphatic hydrocarbon group may contain one heteroatom selected from the group consisting of —NH—, O and S);

Q represents (1) a single bond, (2) an optionally substituted 3- to 8-membered cycloalkylene group, (3) an optionally substituted phenylene group or (4) an optionally substituted 4- to 8-membered divalent heterocyclic group;

$R^{2A}$, $R^{2C}$ and $R^{2D}$ are same or different and each represents a hydrogen atom, alkyl or phenyl, $R^{2B}$ is a hydrogen atom, alkyl, cyano, nitro or phenyl, or a two nitrogen atoms of a guanidino group are cyclized together with one or two of its substituents $R^{2B}$, $R^{2C}$ and $R^{2D}$ to form a saturated or unsaturated 5- or 6-membered ring;

or is taken together as —N($R^1$)—$A^1$—Q—$A^2$—N($R^{2A}$)— to form a 5- to 7-membered ring;

E represents (1) ethenylene, (2) —NRCO—, (3) —NRCONH—, (4) —CONR—, (5) ethynylene, (6) —NRSO$_2$— or (7) aminoalkylene (in which R represents hydrogen or optionally substituted alkyl);

$R^3$ represents an optionally substituted phenyl group or heterocyclic group; and $R^4$ and $R^5$ are (1) same or different and each represents a hydrogen atom, alkyl, alkoxy, aralkyloxy, halogen, nitro, hydroxy, alkoxycarbonyl, —NR$^6$R$^7$, —NR$^6$COR$^7$, —NR$^6$SO$_2$R$^7$, —CONR$^6$R$^7$ (in which $R^6$ and $R^7$ are same or different and each represents a hydrogen atom or alkyl) or (2) when adjacent to each other are taken together to form —O(CH$_2$)$_n$O— (wherein n is an integer of 1 or 2) or —CH=CH—CH=CH—;

or a salt thereof.

2. The compound according to claim 1, wherein $A^1$ and/or $A^2$ is an alkylene which may be substituted by a substituent selected from a group consisting of alkyl, carbamoyl, monoalkylcarbamoyl, dialkylcarbamoyl, hydroxy, alkoxy and trifluoromethyl.

3. The compound according to claim 1, wherein $A^1$ and/or $A^2$ is an alkylene which may be substituted by a substituent selected from a group consisting of alkyl, hydroxy, alkoxy and trifluoromethyl.

4. The compound according to claim 1, wherein Q is a 4- to 8-membered cycloalkylene group which may be substituted by a substituent selected from a group consisting of alkyl, alkoxycarbonyl, carbamoyl, monoalkylcarbamoyl, dialkylcarbamoyl and alkoxy.

5. The compound according to claim 1, wherein Q is a 5- to 7-membered cycloalkylene group which may be substituted by a substituent selected from a group consisting of alkyl, alkoxycarbonyl and alkoxy.

6. The compound according to claim 1, wherein Q is a phenylene group which may be substituted by a substituent selected from a group consisting of alkyl, alkoxy, alkoxycarbonyl, carbamoyl, monoalkylcarbamoyl, dialkylcarbamoyl, sulfamoyl, monoalkylsulfamoyl, dialkylsulfamoyl, amino, monoalkylamino, dialkylamino, nitro, halogen, cyano and trifluoromethyl.

7. The compound according to claim 1, wherein Q is a phenylene group which may be substituted by a substituent selected from a group consisting of alkyl, alkoxy, alkoxycarbonyl, carbamoyl, monoalkylcarbamoyl, dialkylcarbamoyl, amino, monoaklylamino, dialkylamino, nitro, halogen, cyano or trifluoromethyl and trifluoromethyl.

8. The compound according to claim 1, wherein Q is a phenylene group which may be substituted by a substituent selected from a group consisting of alkyl, alkoxy, alkoxycarbonyl, amino, monoalkylamino, dialkylamino, nitro, halogen, cyano or trifluoromethyl and trifluoromethyl.

9. The compound according to claim 1, wherein Q is a 4- to 8-membered divalent heterocyclic group which may be substituted by a substituent selected from a group consisting of alkyl, alkoxy, alkoxycarbonyl, carbamoyl, monoalkylcarbamoyl, dialkylcarbamoyl, amino, monoalkylamino or dialkylamino.

10. The compound according to claim 1, wherein $R^3$ is a phenyl group or heterocyclic group which may be substituted by a substituent selected from a group consisting of alkyl, alkoxy, alkoxycarbonyl, carbamoyl, monoalkylcarbamoyl, dialkylcarbamoyl, sulfamoyl, monoalkylsulfamoyl, dialkylsulfamoyl, alkylsulfonylamino, N-(alkyl)alkylsulfonylamino, amino, monoalkylamino, dialkylamino, nitro, halogen, cyano, hydroxy and trifluoromethyl.

11. The compound according to claim 1, wherein $R^3$ is a phenyl group or heterocyclic group which may be substituted by a substituent selected from a group consisting of alkyl, alkoxy, alkoxycarbonyl, amino, monoalkylamino, dialkylamino, nitro, halogen, cyano, hydroxy and trifluoromethyl.

12. The compound according to claim 1, wherein —N($R^1$)—$A^1$—Q—$A^2$—N($R^{2A}$)— is a 5 to 7-membered ring.

13. The compound according to claim 1, wherein, in the general formula (1), $R^1$ is a hydrogen atom or alkyl, $A^1$ and $A^2$ are same or different and each is (1) a single bond or (2) optionally substituted alkylene, Q is (1) a single bond, (2) an optionally substituted 4- to 8-membered cycloalkylene group (3) an optionally substituted phenylene group or (4) an optionally substituted 5- to 7-membered divalent heterocyclic group, $R^{2A}$, $R^{2B}$, $R^{2C}$ and $R^{2D}$ are same or different and each is a hydrogen atom, alkyl or phenyl, or taken together as —N($R^1$)—$A^1$—Q—$A^2$—N($R^{2A}$)— to form a 5- to 7-membered ring, E is (1) ethenylene, (2) —NRCO— or (3) —CONR—, and $R^4$ and $R^5$ are (1) same or different and each is a hydrogen atom, alkyl, alkoxy, aralkyloxy, halogen, nitro, hydroxy or alkoxycarbonyl or (2) when adjacent to each other are taken together to form —O(CH$_2$)$_n$O— (wherein n is an integer of 1 or 2) or —CH=CH—CH=CH—.

14. The compound according to claim 1, wherein, in the general formula (1), $R^1$ is a hydrogen atom, $A^1$ and $A^2$ are same or different and each is (1) a single bond or (2) optionally substituted alkylene, Q is (1) a single bond, (2) an optionally substituted 5- to 7-membered cycloalkylene group or (3) an optionally substituted phenylene group, $R^{2A}$, $R^{2B}$, $R^{2C}$ and $R^{2D}$ are same or different and each is a hydrogen atom, alkyl or phenyl, E is (1) ethenylene or (2) —NRCO—, and $R^4$ and $R^5$ are same or different and each is a hydrogen atom, alkyl, alkoxy, aralkyloxy, halogen or nitro.

15. The compound according to claim 1, wherein, in the general formula (1), $R^1$ is a hydrogen atom, $A^1$ and $A^2$ are same or different and each is a single bond or optionally substituted alkylene, Q is a single bond or an optionally substituted 5- to 6-membered cycloalkylene group, $R^{2A}$, $R^{2B}$, $R^{2C}$ and $R^{2D}$ are same or different and each is a hydrogen atom or alkyl or taken together as —N($R^1$)—$A^1$—Q—$A^2$—N($R^{2A}$)— to form a 5- to 6-membered ring, E is ethenylene or —NRCO—, and $R^4$ and $R^5$ are same or different and each is a hydrogen atom, alkyl or alkoxy.

16. The compound according to claim 1, wherein the compound is a compound selected from a group consisting of (1S,2R)-N-amidino-2-{[2-(4-chlorobenzoylamino)-6-methoxyquinazolin-4-yl]amino}cyclohexylamine dihydrochloride, N-amidino-2-[6-methoxy-4-{2-[2-(2-pyridyl)ethenyl]quinazolin-4-yl}aminoethyl]phenylethylamine trihydrochloride, cis-4-guanidinomethyl-cis-2-methyl-N-{6-methoxy-2-[2-(2-pyridyl)ethenyl]quinazolin-4-yl}cyclohexylamine trihydrochloride, N-amidino-N'-{6-methyl-2-[2-(2-pyridyl)ethenyl]quinazolin-4-yl}-1,6-hexanediamine trihydrochloride, (1S,2R)-cis-N-amidino-2-{[2-(4-chlorostyryl)-6-methoxyquinazolin-4-yl]amino}cyclohexylamine dihydrochloride and N-amidino-N'-{6-methoxy-2-[2-(2-pyridyl)ethenyl]quinazolin-4-yl}-1,6-hexanediamine trihydrochloride, or a salt thereof.

17. A pharmaceutical composition comprising as an active ingredient a compound represented by the general formula (1) according to claim 1 or a salt thereof.

18. An analgesic comprising as an active ingredient a compound represented by the general formula (1) according to claim 1 or a salt thereof.

* * * * *